US012742013B2

(12) United States Patent
Ward et al.

(10) Patent No.: US 12,742,013 B2
(45) Date of Patent: Sep. 22, 2026

(54) IGF1R ANTIBODIES

(71) Applicant: Horizon Therapeutics Ireland DAC, Dublin (IE)

(72) Inventors: Christopher Davidson Ward, Kensington, MD (US); Martin Jack Borrok, III, North Potomac, MD (US)

(73) Assignee: Horizon Therapeutics Ireland DAC, Dublin (IE)

( * ) Notice: Subject to any disclaimer, the term of this patent is extended or adjusted under 35 U.S.C. 154(b) by 608 days.

(21) Appl. No.: 18/331,535

(22) Filed: Jun. 8, 2023

(65) Prior Publication Data

US 2023/0406942 A1 Dec. 21, 2023

Related U.S. Application Data

(60) Provisional application No. 63/500,168, filed on May 4, 2023, provisional application No. 63/351,077, filed on Jun. 10, 2022.

(51) Int. Cl.
*C07K 16/28* (2006.01)
*A61P 3/00* (2006.01)

(52) U.S. Cl.
CPC ............ *C07K 16/2863* (2013.01); *A61P 3/00* (2018.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,624,821 A | 4/1997 | Winter et al. | |
| 5,648,260 A | 7/1997 | Winter et al. | |
| 5,821,337 A | 10/1998 | Carter et al. | |
| 7,037,498 B2 | 5/2006 | Cohen et al. | |
| 7,317,091 B2 | 1/2008 | Lazar et al. | |
| 7,371,826 B2 | 5/2008 | Presta | |
| 7,572,897 B2 | 8/2009 | Graus et al. | |
| 7,579,157 B2 | 8/2009 | Graus et al. | |
| 7,612,178 B2 | 11/2009 | Hariharan et al. | |
| 7,638,605 B2 | 12/2009 | Ludwig | |
| 7,939,637 B2 | 5/2011 | Raeber et al. | |
| 8,084,582 B2 | 12/2011 | Dahiyat et al. | |
| 8,101,720 B2 | 1/2012 | Lazar et al. | |
| 8,153,121 B2 | 4/2012 | Smith et al. | |
| 8,188,231 B2 | 5/2012 | Lazar et al. | |
| 8,367,805 B2 | 2/2013 | Chamberlain et al. | |
| 8,476,409 B2 | 7/2013 | Baum et al. | |
| 8,546,543 B2 | 10/2013 | Lazar | |
| 10,457,740 B1 | 10/2019 | Kahvejian et al. | |
| 11,208,489 B2 | 12/2021 | Madden et al. | |
| 11,208,490 B2 | 12/2021 | Madden et al. | |
| 12,209,130 B2 | 1/2025 | Madden et al. | |
| 12,286,481 B2 | 4/2025 | Madden et al. | |
| 2005/0014934 A1 | 1/2005 | Hinton et al. | |
| 2007/0218514 A1 | 9/2007 | Smith et al. | |
| 2009/0092614 A1 | 4/2009 | Demarest et al. | |
| 2009/0232828 A1 | 9/2009 | Zhang | |
| 2014/0193415 A1* | 7/2014 | Hosse | C07K 16/2863 435/254.2 |
| 2016/0287611 A1 | 10/2016 | Dobak | |
| 2019/0225696 A1 | 7/2019 | Madden et al. | |
| 2019/0270820 A1 | 9/2019 | Madden et al. | |
| 2021/0253719 A1 | 8/2021 | Sherman et al. | |
| 2021/0284741 A1 | 9/2021 | Madden et al. | |
| 2022/0324985 A1 | 10/2022 | Madden et al. | |
| 2022/0356257 A1 | 11/2022 | Sherman et al. | |
| 2024/0158516 A1* | 5/2024 | Sherman | C07K 16/2863 |
| 2024/0301072 A1 | 9/2024 | Madden et al. | |
| 2024/0352133 A1* | 10/2024 | Bedian | A61P 27/02 |
| 2025/0145723 A1 | 5/2025 | Cao et al. | |
| 2025/0197511 A1* | 6/2025 | Ward | C07K 16/2863 |

FOREIGN PATENT DOCUMENTS

| | | |
|---|---|---|
| WO | WO-9429351 A2 | 12/1994 |
| WO | 2003/106621 A2 | 12/2003 |
| WO | 2005/058967 A2 | 6/2005 |
| WO | 2006/013472 A2 | 2/2006 |
| WO | 2006/069202 A2 | 6/2006 |
| WO | 2014/135611 A1 | 9/2014 |
| WO | 2015/162292 A1 | 10/2015 |
| WO | 2016/064716 A1 | 4/2016 |
| WO | 2021/041773 A1 | 3/2021 |
| WO | 2022/081799 A1 | 4/2022 |
| WO | 2023/019171 A1 | 2/2023 |
| WO | 2023/122714 A2 | 6/2023 |
| WO | 2023/133485 A2 | 7/2023 |
| WO | 2023/133486 A2 | 7/2023 |
| WO | 2023/240223 A2 | 12/2023 |
| WO | WO-2023237928 A2 | 12/2023 |

OTHER PUBLICATIONS

Nakamura and Omasa (J. Bioscience and Bioengineering 2015 120(3): 323-329) (Year: 2015).*
Al-Lazikani et al. Standard conformations for the canonical structures of immunoglobulins. J Mol Biol 273(4):927-948 (1997).
Altschul et al.: Basic local alignment search tool. J. Mol. Biol. 215(3)403-410 (1990).
Berge et al. Pharmaceutical Salts. Journal of Pharmaceutical Sciences 66(1):1-19 (Jan. 1977).
Clarkson et al. Making Antibody Fragments Using Phage Display Libraries. Nature 352:624-628 (1991).
Duncan et al. The binding site for C1q on IgG. Nature 332(6166):738-40 (1988).
Honegger et al. Yet another numbering scheme for immunoglobulin variable domains: an automatic modeling and analysis tool. J Mol Biol 309(3):657-70 (2001).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).

(Continued)

*Primary Examiner* — Peter J Reddig
(74) *Attorney, Agent, or Firm* — Angela L. Purcell

(57) ABSTRACT

Described herein are antibodies that bind and inhibit signaling through the insulin-like growth factor receptor 1.

39 Claims, 3 Drawing Sheets

Specification includes a Sequence Listing.

(56) References Cited

OTHER PUBLICATIONS

Kabat et al. Sequences of Proteins of Immunological Interest. NIH Pub. No. 91-3242. Public Health Service, National Institutes of Health. 1:647-669 (1991).
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87:2264-2268 (1990).
Kindt et al,. Kuby Immunology, 6th ed., W.H. Freeman and Co., p. 91 (2007).
Lefranc et al. IMGT unique numbering for immunoglobulin and T cell receptor variable domains and Ig superfamily V-like domains. Dev Comp Immunol 27(1):55-77 (2003).
Maccallum et al. Antibody-antigen interactions: contact analysis and binding site topography. J Mol Biol. 262(5):732-745 (1996).
Portolano et al., Lack of promiscuity in autoantigen-specific H and L chain combinations as revealed by human H and L chain "roulette". J. Immunol. 150:880-887 (1993).
Whitelegg et al. WAM: an improved algorithm for modelling antibodies on the WEB. Protein Eng. 13:819-24 (2000).
Burtrum et al., A Fully Human Monoclonal Antibody to the Insulin-like Growth Factor I Receptor Blocks Ligand-dependent Signaling and Inhibits Human Tumor Growth in Vivo. Cancer Research 63:8912-8921 (2003).
Dall'Acqua et al., Properties of Human IgG1s Engineered for Enhanced Binding to the Neonatal Fc Receptor (FcRn). Journal of Biological Chemistry 281(33): 23514-23524 (2006).
Dondelinger et al., Understanding the Significance and Implications of Antibody Numbering and Antigen-Binding Surface/Residue Definition. Frontiers in Immunology 9(2278):1-15 (2018).
Osher et al., Therapeutic Targeting of the IGF Axis. Cells 8(8):1-25 (2019).
PCT/IB2023/000335 International Search Report and Written Opinion dated Jan. 11, 2024.
Rudikoff et al. Single Amino Acid Substitution Altering Antigen-binding Specificity. PNAS USA 79(6):1979-1983 (1982).
Winkler, et al. Changing the Antigen Binding Specificity by Single Point Mutations of an Anti-p24 (HIV-1)Antibody. The Journal of Immunology. 165(8):4505-4514 (2000).
Mourits et al., "Clinical activity score as a guide in the management of patients with Graves' ophthalmopathy," Clinical Endocrinology, vol. 47(1), pp. 9-14 (1997).
Mourits et al., "Clinical criteria for the assessment of disease activity in Graves' ophthalmopathy: a novel approach," Br. J. Ophthalmol., vol. 73(8), pp. 639-644 (1989).
Naik et al., "Immunopathogenesis of thyroid eye disease: emerging paradigms," Surv. Ophthalmol., vol. 55(3), pp. 215-226 (2010).
NCT06248619, May 22, 2025 version, accessed Jun. 16, 2025.
Palowski et al., "Decreased Frequencies of Peripheral Blood CD4+ CD25+CD127-Foxp3+ in Patients with Graves' Disease and Graves' Orbitopathy: Enhancing Effect of Insulin Growth Factor-1 on Treg Cells," Horm. Metab. Res., vol. 49(3), pp. 185-191 (2017).
Pappo et al., "R1507, a Monoclonal Antibody to the Insulin-Like Growth Factor 1 Receptor, in Patients With Recurrent or Refractory Ewing Sarcoma Family of Tumors: Results of a Phase II Sarcoma Alliance for Research Through Collaboration Study," J. Clin. Oncol., vol. 29(34), pp. 4541-4547 (2011).
Patel et al., "A New Era in the Treatment of Thyroid Eye Disease," American Journal of Ophthalmology, vol. 208: pp. 281-288 (2019).
Piantanida, E. et al., "Teprotumumab: A New Avenue for the Management of Moderate-to-Severe and Active Graves' Orbitopathy?", J Endocrinol Invest., 40(8):885-7, (2017).
Place et al. Inhibiting thyrotropin/insulin-like growth factor 1 receptor crosstalk to treat Graves' ophthalmopathy: studies in orbital fibroblasts in vitro. Br J Pharmacol. 174(4):328-340 (2017).
Pritchard et al., "Igs from patients with Graves' disease induce the expression of T cell chemoattractants in their fibroblasts," J. Immunol., vol. 168(2), pp. 942-950 (2002).
Pritchard et al., "Immunoglobulin activation of T cell chemoattractant expression in fibroblasts from patients with Graves' disease is mediated through the insulin-like growth factor I receptor pathway," J. Immunol., vol. 170(12), pp. 6348-6354 (2003).
Ramalingam et al., "Randomized Phase II Study of Erlotinib in Combination with Placebo or R1507, a Monoclonal Antibody to Insulin-Like Growth Factor-1 Receptor, for Advanced-Stage Non-Small-Cell Lung Cancer," J. Clin. Oncol., 29(34), pp. 4574-4580 (2011).
Salvi et al. Efficacy of B-cell targeted therapy with rituximab in patients with active moderate to severe Graves' orbitopathy: a randomized controlled study. J Clin Endocrinol Metab. 100(2):422-31 (2015).
Salvi, "Immunotherapy for Graves' ophthalmopathy," Curr. Opin. Endocrinol. Diabetes Obes., vol. 21(5), pp. 409-414 (2014).
Sanderson et al. BI 885578 a Novel IGF1 R/INSR Tyrosine Kinase Inhibitor with Pharmacokinetic Properties That Dissociate Antitumor Efficacy and Perturbation of Glucose Homeostasis. Mol Cancer Ther 14(12):2762-72 (2015).
Sanofi-Aventis Group, "Synopsis Style Clinical Study Report", AVE1642-TED6421, Version No. 1, Mar. 4, 2011, pp. 1-12.
Smith et al. Role of insulin-like growth factor-1 (IGF-1) pathway in the pathogenesis of Graves' orbitopathy. Best Pract Res Clin Endocrinol Metab. 3:291-302 (2012).
Smith et al. Unique attributes of orbital fibroblasts and global alterations in IGF-1 receptor signaling could explain thyroid-associated ophthalmopathy. Thyroid. 18(9):983-8 (2008).
Smith et al., "Building the Case for Insulin-Like Growth Factor Receptor-I Involvement in Thyroid-Associated Ophthalmopathy," Frontiers in Endocrinology, vol. 7(167), pp. 1-8 (2017).
Smith et al., "Immunoglobulins from Patients with Graves' Disease Induce Hyaluronan Synthesis in Their Orbital Fibroblasts through the Self-Antigen, Insulin-Like Growth Factor-I Receptor," J Clin Endocrinol Metab., vol. 89(10), pp. 5076-5080 (2004).
Smith et al., "Insulin-Like Growth Factor-I Regulation of Immune Function: A Potential Therapeutic Target in Autoimmune Diseases?" Pharmacological Rev., vol. 62(2), pp. 199-236 (2010).
Smith et al., "New Advances in Understanding Thyroid-Associated Ophthalmopathy and the Potential Role for Insulin-Like Growth Factor-I Receptor [version 1; referees: 2 approved]," F1000 Research 2018, 7(F1000 Faculty Rev): 134, pp. 1-9 (Last Updated Feb. 1, 2018).
Smith et al., "Pathogenesis of Graves' orbitopathy: A 2010 update," J. Endocrinol. Invest., vol. 33(6), pp. 414-421 (2010).
Smith et al., "Teprotumumab for Thyroid-Associated Ophthalmopathy," New England Journal of Medicine, vol. 376 (18), pp. 1749-1761 (2017).
Smith, "Recognizing the Putative Role for TSH Receptor Expressing Fibrocytes in Thyroid-Associated Ophthalmopathy may solve several mysteries," Nat. Rev. Endocrinol., vol. 11(3), pp. 171-181 (2015).
Solomon-Zemler et al., "Nuclear insulin-like growth factor-1 receptor (IGF1R) displays proliferative and regulatory activities in non-malignant cells", Plos One, Sep. 25, 2017, 14 pages.
Song et al. "Locally produced insulin-like growth factor-1 by orbital fibroblasts as implicative pathogenic factor rather than systemically circulated IGF-1 for patients with thyroid-associated ophthalmopathy," Graefes Arch Clin Exp Ophthalmol., vol. 250(3), pp. 433-440 (2012).
Stan et al., "Randomized controlled trial of rituximab in patients with Graves' orbitopathy," J. Clin. Endocrinol. Metab., vol. 100(2), pp. 432-431 (2015).
Terwee et al. Development of a disease specific quality of life questionnaire for patients with Graves' ophthalmopathy: the GO-QoL. Br J Ophthalmol. 82(7):773-9 (1998).
Titze et al. An allometric pharmacokinetic/pharmacodynamics model for BI 893923 a novel IGF-1 receptor inhibitor. Cancer Chemother Pharmacol 79(3):545-558 (2017).
Tsui et al. Evidence for an association between thyroid-stimulating hormone and insulin-like growth factor 1 receptors: a tale of two antigens implicated in Graves' disease. J Immunol. 181(6):4397-405 (2008).

(56) References Cited

OTHER PUBLICATIONS

Ugradar et al. Teprotumumab for non-inflammatory thyroid eye disease (TED): evidence for increased IGF-1R expression. Eye (Lond) 35(9):2607-2612 (2021).
Ugradar et al., "Teprotumumab for the treatment of chronic thyroid eye disease", Eye (Lond), vol. 36, No. 8, 2022, pp. 1553-1559.
Varewijck et al., "Circulating IgGs may modulate IGF-I receptor stimulating activity in a subset of patients with Graves' ophthalmopathy," J. Clin. Endocrinol. Metab., vol. 98(2), pp. 769-776 (2013).
Wang et al., "Drugging IGF-1R in cancer: New insights and emerging opportunities", Genes & Diseases, vol. 10, No. 1, Jan. 2023, pp. 199-211.
Weightman et al., "Autoantibodies to IGF-1 binding sites in thyroid associated ophthalmopathy," Autoimmunity, vol. 16(4), pp. 251-257 (1993).
Werner, "Classification of the eye changes of Graves' disease," Am. J. Ophthalmol., vol. 68(4), pp. 646-648 (1969).
Werner, "Modification of the classification of the eye changes of Graves' disease," Am. J. Ophthalmol., vol. 83(5), pp. 725-727 (1977).
Wiersinga, "Management of Graves' ophthalmopathy," Endocrinology & Metabolism, vol. 3(5), pp. 396-404 (2007).
Wiersinga, W. M. et al., "Clinical assessment of patients with Graves' orbitopathy: the European Group on Graves' Orbitopathy recommendations to generalists, specialists and clinical researchers", European Journal of Endocrinology, 2006, vol. 155, pp. 387-389.
Xu et al., "Comparative Efficacy of Medical Treatments for Thyroid Eye Disease: A Network Meta-Analysis," J. Ophthalmol., vol. 2018, 7184163, pp. 1-10 (2018).
Xu et al., "Ocular Surface Characteristics and Impression Cytology in Patients with Active versus Inactive Thyroid Eye Disease," Eye Science, vol. 27(2), pp. 64-68 (2012).
Xue et al., "Insulin-like growth factor-1 receptor (IGF-1R) kinase inhibitors in cancer therapy: advances and perspectives," Curr. Pharm. Des., vol. 18(20), pp. 2901-2913 (2012).
Zhang, L, et al., "Possible Targets for Nonimmunosuppressive Therapy of Graves' Orbitopathy", J Clin Endocrinol Metab. 99(7):E1183-90 (2014).
Zhao et al., "Insulin-like growth factor 1 promotes to the proliferation and adipogenesis of orbital adipose-derived stromal cells in thyroid-associated ophthalmopathy," Exp. Eye Res., vol. 107, pp. 65-73 (2013).
Bagatell et al., "Pharmacokinetically Guided Phase 1 Trial of the IGF-1 Receptor Antagonist RG1507 in Children with Recurrent or Refractory Solid Tumors," Clin. Cancer Res., 17(3), pp. 611-619 (2011).
Bahn, R. S., "Current Insights into the Pathogenesis of Graves' Ophthalmopathy", Horm Metab Res., vol. 47(10), pp. 773-778 (2015).
Bahn, R. S., "Graves' ophthalmopathy", N Engl J Med., vol. 362(8), pp. 726-738 (2010).
Bartalena et al., "Consensus statement of the European Group on Graves' orbitopathy (EUGOGO) on management of GO," Eur. J. Endocrinol., vol. 158(3), pp. 273-285 (2008).
Bartalena et al., "Efficacy and safety of three different cumulative doses of intravenous methylprednisolone for moderate to severe and active Graves' orbitopathy," J. Clin. Endocrinol. Metab., vol. 97(12), pp. 4454-4463 (2012).
Bartalena et al., "The 2016 European Thyroid Association/European Group on Graves' Orbitopathy Guidelines for the Management of Graves' Orbitopathy", Eur Thyroid J., vol. 5, No. 1, 2016, pp. 9-26.
Calzone et al., "Epitope-specific mechanisms of IGF1R inhibition by ganitumab", Plos One, vol. 8, No. 2, 2013, 15 pages.
Chen et al., "Effects and Its Mechanism of IGF-1R on the Synthesis of Hyaluronic Acid in Orbital Fibroblasts of Thyroid Associated Ophthalmopathy," Sichuan Da Xue Xue Bao Yi Xue Ban, vol. 48(5), pp. 727-731 (2017).
Chen et al., "IGF-1R as an anti-cancer target—trials and tribulations", Chin J Cancer., vol. 32, No. 5, May 2013, pp. 242-252.
Chen et al., "Teprotumumab, an IGF-1R blocking monoclonal antibody inhibits TSH and IGF-1 action in fibrocytes," J Clin Endocrinol Metab., vol. 99(9), pp. E1635-E1640 (2014).
Clinical Trial No. NCT04583735. A Study Evaluating TEPEZZA® Treatment in Patients With Chronic (Inactive) Thyroid Eye Disease, Version 1. Reported date submitted: Oct. 6, 2020. Reported date first posted: Oct. 12, 2020. Date accessed: Sep. 28, 2025.
Clinical Trial No. NCT04583735. A Study Evaluating TEPEZZA® Treatment in Patients With Chronic (Inactive) Thyroid Eye Disease, Version 2. Reported date submitted: Aug. 5, 2021. Reported date update posted: Aug. 6, 2021. Date accessed: Sep. 28, 2025.
Clinical Trials No. NCT01868997. Teprotumumab (RV 001) Treatment in Patients With Active Thyroid Eye Disease, Version 22. Reported date submitted: Mar. 27, 2018. Date publicly available: Unknown. Date accessed: May 24, 2024.
Clinical Trials No. NCT03298867, "Treatment of Graves' Orbitopathy (Thyroid Eye Disease) to Reduce Proptosis With Teprotumumab Infusions in a Randomized, Placebo-Controlled, Clinical Study (OPTIC)", Retrieved from Internet: https://clinicaltrials.gov/study/NCT03298867, pp. 1-16(2024).
Crudden et al., "Below the Surface: IGF-1R Therapeutic Targeting and Its Endocytic Journey", Cells, vol. 8, No. 10, 2019, 23 pages.
Degorce et al., "Discovery of a Potent Selective Orally Bioavailable and Efficacious Novel 2-(Pyrazol-4-ylamino)-pyrimidine Inhibitor of the Insulin-like Growth Factor-1 Receptor (IGF-1R)," J. Med. Chem., vol. 59(10), pp. 4859-4866 (2016).
Doern et al., "Characterization of Inhibitory Anti-insulin-like Growth Factor Receptor Antibodies with Different Epitope Specificity and Ligand-blocking Properties", JBC, vol. 284, No. 15, Apr. 2009 pp. 10254-10267.
Dolman et al., "Evaluating Graves' orbitopathy," Best Pract. Res. Clin. Endocrinol. Metab., vol. 26(3), pp. 229-248 (2012).
Dolman et al., "VISA Classification for Graves orbitopathy," Ophthalmic Plast. Reconstr. Surg., vol. 22(5), pp. 319-324 (2006).
Douglas et al., "Aberrant expression of the insulin-like growth factor-1 receptor by T cells from patients with Graves' disease may carry functional consequences for disease pathogenesis," J. Immunol., vol. 178(5), pp. 3281-3287 (2007).
Douglas et al., "B cells from patients with Graves' disease aberrantly express the IGF-1 receptor: implications for disease pathogenesis," J. Immunol., vol. 181(8), pp. 5768-5774 (2008).
Douglas et al., "Efficacy and Safety of Teprotumumab in Patients With Thyroid Eye Disease of Long Duration and Low Disease Activity," The Journal of Clinical Endocrinology & Metabolism, vol. 109(1), pp. 25-35 (2024).
Douglas et al., "Increased generation of fibrocytes in thyroid-associated ophthalmopathy," J. Clin. Endrocrinol. Metab., vol. 95(1), pp. 430-438 (2010).
Douglas et al., "Teprotumumab for the Treatment of Active Thyroid Eye Disease," N. Engl. J. Med., vol. 382, pp. 341-352 (2020).
Douglas, R., "Teprotumumab, an Insulin-Like Growth Factor-1 Receptor Antagonist Antibody, in the Treatment of Active Thyroid Eye Disease: A Focus on Proptosis", Eye (Lond), vol. 33(2), pp. 183-190 (2019).
Ezra et al., "Genome Level Microarray Expression Profiling Implicates IGF-1 and Wnt Signalling Dysregulation in the Pathogenesis of Thyroid Associated Ophthalmopathy," ARVO Annual Meeting Scientific Abstracts, Invest. Ophthalmol. Vis. Sci., vol. 52, 5100, pp. 1-2 (2011).
Gianoukakis et al. Immunoglobulin G from patients with Graves' disease induces interleukin-16 and RANTES expression in cultured human thyrocytes: a putative mechanism for T-cell infiltration of the thyroid in autoimmune disease. Endocrinology. 147(4):1941-9 (2006).
Görtz et al., "Pathogenic Phenotype of Adipogenesis and Hyaluronan in Orbital Fibroblasts from Female Graves' Orbitopathy Mouse Model," Endocrinology, vol. 157(10), pp. 3771-3778 (2016).
Gupta, "Intention-to-treat concept: A review," Perspect. Clin. Res., vol. 2(3), pp. 109-112 (2011).
Haim Werner, "The IGF1 Signaling Pathway: From Basic Concepts to Therapeutic Opportunities", Int. J. Mol. Sci., vol. 24, No. 19, 2023, 13 pages.
Hansson, "Aspects of growth factors in exophthalmos," Acta Endocrinologica (Cophen), vol. 121 (Suppl 2), pp. 107-111 (1989).

(56) References Cited

OTHER PUBLICATIONS

Hoa et al., "Nuclear Targeting of IGF-1 Receptor in Orbital Fibroblasts from Graves' Disease: Apparent Role of ADAM17," PLoS One, vol. 7(4), e34173, pp. 1-9 (2012).
Hwang et al., "Orbital fibroblasts from patients with thyroid-associated ophthalmopathy overexpress CD40: CD154 hyperinduces IL-6, IL-8, and MCP-1," Invest. Ophthalmol. Vis. Sci., vol. 50(5), pp. 2262-2268 (2008).
Imai et al., "Effect of growth factors on hyaluronan and proteoglycan synthesis by retroocular tissue fibroblasts of Graves' ophthalmopathy in culture," Acta Endocrinol (Copenh), vol. 126(6), pp. 541-552 (1992).
Kahaly et al. Highlighted Oral 2, abstract presented at the American Thyroid Association (ATA) 88th Annual Meeting, Washington, DC, Oct. 3-8, 2018.
Khong et al., "Pathogenesis of thyroid eye disease: review and update on molecular mechanisms," Br. J. Ophthalmol., vol. 100(1), pp. 142-150 (2016).
Khoo et al., "Pathogenesis of Graves' Ophthalmopathy: The Role of Autoantibodies," Thyroid, vol. 17(10), pp. 1013-1018 (2007).
Krieger et al. Thyroid Stimulating Hormone (TSH)/Insulin-like Growth Factor 1 (IGF1) Receptor Cross-talk in Human Cells. Curr Opin Endocr Metab Res. 2:29-33 (2018).
Krieger et al. TSH/IGF-1 Receptor Cross-Talk Rapidly Activates Extracellular Signal-Regulated Kinases in Multiple Cell Types. Endocrinology. 158(10):3676-3683 (2015).
Krieger et al., "TSHR/IGF-1R Cross-Talk, Not IGF-R Stimulating Antibodies, Mediates Graves' Ophthalmopathy Pathogenesis," Thyroid, vol. 27(5), pp. 746-747 (2017).
Kuenkele et al., "Abstract LB-397: Functional characterization of IGF-1R antibodies and possible implications for clinical safety and efficacy ", Cancer Res., vol. 71, No. 8, 2011, 2 pages.
Kumar et al. A stimulatory thyrotropin receptor antibody enhances hyaluronic acid synthesis in Graves' orbital fibroblasts: inhibition by an IGF-I receptor blocking antibody. J Clin Endocrinol Metab. 97(5):1681-7 (2012).
Kumar et al. Forkhead Transcription Factor FOXO1 Is Regulated by Both a Stimulatory Thyrotropin Receptor Antibody and Insulin-Like Growth Factor-1 in Orbital Fibroblasts from Patients with Graves' Ophthalmopathy. Thyroid 25(10):1145-50 (2015).
Kurzrock et al., "A Phase I Study of Weekly R1507, A Human Monoclonal Antibody Insulin-like Growth Factor-I Receptor Antagonist, in Patients with Advanced Solid Tumors," Clin. Cancer Res., vol. 16(8), pp. 2458-2465 (2010).
Lovell et al., "Adalimumab with or without Methotrexate in Juvenile Rheumatoid Arthritis," N. Engl. J. Med., vol. 359, pp. 810-820 (2008).
Ma et al., "The adverse events profile of anti-IGF-1R monoclonal antibodies in cancer therapy," Br J Clin Pharmacol, vol. 77(6), pp. 917-928 (2013).
Mao et al., "Polyubiquitination of Insulin-like Growth Factor I Receptor (IGF-IR) Activation Loop Promotes Antibody-induced Receptor Internalization and Down-regulation", JBC, vol. 286, No. 48, Dec. 2, 2011, pp. 41852-41861.
Marcus-Samuels, "Evidence That Graves' Ophthalmopathy Immunoglobulins Do Not Directly Activate IGF-1 Receptors," Thyroid, vol. 28(5), pp. 650-655 (2018).
Martins et al., "IGF1R Signaling in Ewing Sarcoma Is Shaped by Clathrin-/Caveolin-Dependent Endocytosis", Plos One, May 17, 2011, 12 pages.
Mehren et al., "A phase 1, open-label, dose-escalation study of BIIB022 (anti-IGF-1R monoclonal antibody) in subjects with relapsed or refractory solid tumors", Investigational New Drugs, vol. 3, 2014, pp. 518-525.

* cited by examiner

```
B09_VH            QVELVESGGGVVQPGRSQRLSCAASGFTFSSHGMHWVRQAPGKGLEWVAIIAGDASTTYY
B02_VH            QVELVESGGGVVQPGRSQRLSCAASGFTFSSTGMHWVRQAPGKGLEWVAYIWFDGSSTYY
C10_VH            QVELVESGGGVVQPGRSQRLSCAASGFTFSSAGMHWVRQAPGKGLEWVAIIWADGSSTYY
D10_VH            QVELVESGGGVVQPGRSQRLSCAASGFTFSSYGMHWVRQAPGKGLEWVAIINFDGSSTYY
Teprotumumab_VH   QVELVESGGGVVQPGRSQRLSCAASGFTFSSYGMHWVRQAPGKGLEWVAIIWFDGSSTYY
E01_VH            QVELVESGGGVVQPGRSQRLSCAASGFTFSSYGMHWVRQAPGKGLEWVAIIWFDGSSTYY
H11_VH            QVELVESGGGVVQPGRSQRLSCAASGFTFSSYGMHWVRQAPGKGLEWVATIWHDGSSTYY
B10_VH            QVELVESGGGVVQPGRSQRLSCAASGFTFSSYGMHWVRQAPGKGLEWVATIWFDGSSTYY
A11_VH            QVELVESGGGVVQPGRSQRLSCAASGFTFSSYGMHWVRQAPGKGLEWVAYIWFDGSSTYY
F02_VH            QVELVESGGGVVQPGRSQRLSCAASGFTFSSHGMHWVRQAPGKGLEWVATIWFDGSSTYY
D03_VH            QVELVESGGGVVQPGRSQRLSCAASGFTFSSHGMHWVRQAPGKGLEWVAYIWFDGSSTYY
                  ****************************** ****************** *  *.*:***

B09_VH            ADSVRGRFTISRDNSKNTLYLQMNSLRAEDTAVYFCARELGRRYFDLWGRGTLVSVSS
B02_VH            ADSVRGRFTISRDNSKNTLYLQMNSLRAEDTAVYFCARELNRRYFDLWGRGTLVSVSS
C10_VH            ADSVRGRFTISRDNSKNTLYLQMNSLRAEDTAVYFCARELGRRYFDLWGRGTLVSVSS
D10_VH            ADSVRGRFTISRDNSKNTLYLQMNSLRAEDTAVYFCARELGRRYFDLWGRGTLVSVSS
Teprotumumab_VH   ADSVRGRFTISRDNSKNTLYLQMNSLRAEDTAVYFCARELGRRYFDLWGRGTLVSVSS
E01_VH            ADSVRGRFTISRDNSKNTLYLQMNSLRAEDTAVYFCARELGRRYFDLWGRGTLVSVSS
H11_VH            ADSVRGRFTISRDNSKNTLYLQMNSLRAEDTAVYFCARELGRRYFDLWGRGTLVSVSS
B10_VH            ADSVRGRFTISRDNSKNTLYLQMNSLRAEDTAVYFCARELGRRYFDLWGRGTLVSVSS
A11_VH            ADSVRGRFTISRDNSKNTLYLQMNSLRAEDTAVYFCARELGRRYFDLWGRGTLVSVSS
F02_VH            ADSVRGRFTISRDNSKNTLYLQMNSLRAEDTAVYFCARELGRRYFDLWGRGTLVSVSS
D03_VH            ADSVRGRFTISRDNSKNTLYLQMNSLRAEDTAVYFCARELGRRYFDLWGRGTLVSVSS
                  ****************************************.*****************
```

FIG. 1A

```
H11_VL            EIVLTQSPATLSLSPGERATLSCRASQSVSSALAWYQQKPGQAPRLLIYDASKRATGIPA
F02_VL            EIVLTQSPATLSLSPGERATLSCRASQSVSSTLAWYQQKPGQAPRLLIYDASKRATGIPA
D03_VL            EIVLTQSPATLSLSPGERATLSCRASQSVSSALAWYQQKPGQAPRLLIYDASKRATGIPA
Teprotumumab_VL   EIVLTQSPATLSLSPGERATLSCRASQSVSSYLAWYQQKPGQAPRLLIYDASKRATGIPA
B02_VL            EIVLTQSPATLSLSPGERATLSCRASQSVSSYLAWYQQKPGQAPRLLIYDASKRATGIPA
B09_VL            EIVLTQSPATLSLSPGERATLSCRASQSVSSYLAWYQQKPGQAPRLLIYDASKRATGIPA
E01_VL            EIVLTQSPATLSLSPGERATLSCRASQSVSSYLAWYQQKPGQAPRLLIYDASKRATGIPA
B10_VL            EIVLTQSPATLSLSPGERATLSCRASQSVSSYLAWYQQKPGQAPRLLIYDASKRATGIPA
D10_VL            EIVLTQSPATLSLSPGERATLSCRASQSVSSYLAWYQQKPGQAPRLLIYDASKRATGIPA
C10_VL            EIVLTQSPATLSLSPGERATLSCRASQSVSSYLAWYQQKPGQAPRLLIYDASKRATGIPA
A11_VL            EIVLTQSPATLSLSPGERATLSCRASQSVSSYLAWYQQKPGQAPRLLIYDASKRATGIPA
                  ******************************* ****************************

H11_VL            RFSGSGSGTDFTLTISSLEPEDFAVYYCQQRGKYPPWTFGQGTKVESK
F02_VL            RFSGSGSGTDFTLTISSLEPEDFAVYYCQQRSKYPPWTFGQGTKVESK
D03_VL            RFSGSGSGTDFTLTISSLEPEDFAVYYCQQRSKYPPWTFGQGTKVESK
Teprotumumab_VL   RFSGSGSGTDFTLTISSLEPEDFAVYYCQQRSKWPPWTFGQGTKVESK
B02_VL            RFSGSGSGTDFTLTISSLEPEDFAVYYCQQRSKYPPWTFGQGTKVESK
B09_VL            RFSGSGSGTDFTLTISSLEPEDFAVYYCQQRSKYPPWTFGQGTKVESK
E01_VL            RFSGSGSGTDFTLTISSLEPEDFAVYYCQQRSKYPPWTFGQGTKVESK
B10_VL            RFSGSGSGTDFTLTISSLEPEDFAVYYCQQRSKYPPWTFGQGTKVESK
D10_VL            RFSGSGSGTDFTLTISSLEPEDFAVYYCQQRSKYPPWTFGQGTKVESK
C10_VL            RFSGSGSGTDFTLTISSLEPEDFAVYYCQQRSKYPPWTFGQGTKVESK
A11_VL            RFSGSGSGTDFTLTISSLEPEDFAVYYCQQRSKYPPWTFGQGTKVESK
                  *******************************.*:**************
```

FIG. 1B

IGF1R ANTIBODIES

CROSS REFERENCE

This application claims the benefit of U.S. Provisional App. No. 63/500,168 filed May 4, 2023, and U.S. Provisional App. No. 63/351,077 filed Jun. 10, 2022, both of which are incorporated by reference herein in their entirety.

SEQUENCE LISTING

The instant application contains a Sequence Listing which has been submitted electronically in XML format and is hereby incorporated by reference in its entirety. Said XML copy, created on Aug. 29, 2023, is named "58651825201_SL.xml" and is 51,646 bytes in size.

SUMMARY

Subcutaneous administration of antibody treatments to a patient is a more convenient and cost-effective delivery route than intravenous administration since such treatments can be administered at home, and do not require the presence of a trained medical specialist. One hurdle to subcutaneous administration of antibodies, however, is the substantial reduction in volume of an antibody formulation to be used in a pre-filled syringe, onbody infusor, autoinjector, etc. To address this, high concentration antibody formulations are needed but this may be impractical for subcutaneous delivery due to viscosity challenges, aggregation behavior and other aggravating factors to formulate large molecules. One solution is the use of novel antibodies that bind a target with higher affinity or that exert higher biological activity than known antibodies. Additionally, antibodies comprising certain Fc region mutations possess longer half-life in vivo, can further reduce the amount of antibody to be included in a subcutaneous formulation.

Described herein are IGF1R antibodies with high binding affinities and high biological inhibitory activity. Also, described herein are IGF1R antibodies with extended half-life and low levels of ADCC activity. Such antibodies can be effectively included in formulations for subcutaneous administration to improve ease of administration for patients. Described herein in one aspect is an antibody or antigen binding fragment thereof that binds insulin like growth factor 1 receptor (IGF1R), wherein the antibody or antigen binding fragment thereof comprises: (a) an immunoglobulin heavy chain CDR1 (HCDR1) comprising the amino acid sequence $SX_1GMH$ (SEQ ID NO: 53), wherein $X_1$ is H, Y, A, or T; (b) an immunoglobulin heavy chain CDR2 (HCDR2) comprising the amino acid sequence $X_1IX_2X_3DX_4SX_5TYYADSVRG$ (SEQ ID NO: 54), wherein $X_1$ is I, T, or Y, $X_2$ is W, N, or A, $X_3$ is F, H, A, or G, $X_4$ is G or A, $X_5$ is S or T; (c) an immunoglobulin heavy chain CDR3 (HCDR3) comprising the amino acid sequence $ELX_1RRYFDL$ (SEQ ID NO: 55), wherein $X_1$ is G or N; (d) an immunoglobulin light chain CDR1 (LCDR1) comprising the amino acid sequence $RASQSVSSX_1LA$ (SEQ ID NO: 56), wherein $X_1$ is Y, A, or T; (e) an immunoglobulin light chain CDR2 (LCDR2) comprising the amino acid sequence DASKRAT (SEQ ID NO: 46); and/or an immunoglobulin light chain CDR3 (LCDR3) comprising the amino acid sequence $QQRX_1KX_2PPWT$ (SEQ ID NO: 57), wherein $X_1$ is S or G, $X_2$ is Y or W; wherein the antibody or antigen binding fragment thereof does not comprise an immunoglobulin heavy chain variable region identical to SEQ ID NO: 1 and/or an immunoglobulin light chain variable region identical to SEQ ID NO: 2. In one embodiment, the antibody or antigen binding fragment thereof that binds insulin like growth factor 1 receptor (IGF1R), wherein the antibody or antigen binding fragment thereof comprises: (a) an immunoglobulin heavy chain CDR1 (HCDR1) comprising the amino acid sequence $SX_1GMH$ (SEQ ID NO: 53), wherein $X_1$ is H, Y, A, or T; (b) an immunoglobulin heavy chain CDR2 (HCDR2) comprising the amino acid sequence $X_1IX_2X_3DX_4SX_5TYYADSVRG$ (SEQ ID NO: 54), wherein $X_1$ is I, T, or Y, $X_2$ is W, N, or A, $X_3$ is F, H, A, or G, $X_4$ is G or A, $X_5$ is S or T; (c) an immunoglobulin heavy chain CDR3 (HCDR3) comprising the amino acid sequence $ELX_1RRYFDL$ (SEQ ID NO: 55), wherein $X_1$ is G or N; (d) an immunoglobulin light chain CDR1 (LCDR1) comprising the amino acid sequence $RASQSVSSX_1LA$ (SEQ ID NO: 56), wherein $X_1$ is Y, A, or T; (e) an immunoglobulin light chain CDR2 (LCDR2) comprising the amino acid sequence DASKRAT (SEQ ID NO: 46); and/or an immunoglobulin light chain CDR3 (LCDR3) comprising the amino acid sequence $QQRX_1KX_2PPWT$ (SEQ ID NO: 57), wherein $X_1$ is S or G, $X_2$ is Y or W; wherein the antibody or antigen binding fragment thereof does not comprise an immunoglobulin heavy chain variable region identical to SEQ ID NO: 1 and an immunoglobulin light chain variable region identical to SEQ ID NO: 2. In certain embodiments, the antibody or antigen binding fragment thereof comprises an immunoglobulin heavy chain CDR1 (HCDR1), n immunoglobulin heavy chain CDR2 (HCDR2), an immunoglobulin heavy chain CDR3 (HCDR3), an immunoglobulin light chain CDR1 (LCDR1) an immunoglobulin light chain CDR2 (LCDR2), and/or an immunoglobulin light chain CDR3 (LCDR3), wherein: (a) the HCDR1 comprises the amino acid sequence SHGMH (SEQ ID NO: 30); (b) the HCDR2 comprises the amino acid sequence YIWFDGSSTYYADSVRG (SEQ ID NO: 35); (c) the HCDR3 comprises the amino acid sequence ELGRRYFDL (SEQ ID NO: 41); (d) the LCDR1 comprises the amino acid sequence RASQSVSSALA (SEQ ID NO: 43); (e) the LCDR2 comprises the amino acid sequence DASKRAT (SEQ ID NO: 46); and/or (f) the LCDR3 comprises the amino acid sequence QQRSKYPPWT (SEQ ID NO: 48). In certain embodiments, the antibody or antigen binding fragment thereof comprises an immunoglobulin heavy chain CDR1 (HCDR1), n immunoglobulin heavy chain CDR2 (HCDR2), an immunoglobulin heavy chain CDR3 (HCDR3), an immunoglobulin light chain CDR1 (LCDR1) an immunoglobulin light chain CDR2 (LCDR2), and/or an immunoglobulin light chain CDR3 (LCDR3), wherein: (a) the HCDR1 comprises the amino acid sequence SYGMH (SEQ ID NO: 33); (b) the HCDR2 comprises the amino acid sequence IIWFDGSSTYYADSVRG (SEQ ID NO: 38); (c) the HCDR3 comprises the amino acid sequence ELGRRYFDL (SEQ ID NO: 41); (d) the LCDR1 comprises the amino acid sequence RASQSVSSYLA (SEQ ID NO: 45); (e) the LCDR2 comprises the amino acid sequence DASKRAT (SEQ ID NO: 46); and/or (f) the LCDR3 comprises the amino acid sequence QQRSKYPPWT (SEQ ID NO: 48). In certain embodiments, the antibody or antigen binding fragment thereof comprises an immunoglobulin heavy chain CDR1 (HCDR1), n immunoglobulin heavy chain CDR2 (HCDR2), an immunoglobulin heavy chain CDR3 (HCDR3), an immunoglobulin light chain CDR1 (LCDR1) an immunoglobulin light chain CDR2 (LCDR2), and/or an immunoglobulin light chain CDR3 (LCDR3), wherein: (a) the HCDR1 comprises the amino acid sequence SHGMH (SEQ ID NO: 30); (b) the HCDR2 comprises the amino acid sequence IIAGDASTTYYADSVRG (SEQ ID NO: 34); (c)

the HCDR3 comprises the amino acid sequence ELGR-RYFDL (SEQ ID NO: 41); (d) the LCDR1 comprises the amino acid sequence RASQSVSSYLA (SEQ ID NO: 45); (e) the LCDR2 comprises the amino acid sequence DASK-RAT (SEQ ID NO: 46); and/or (f) the LCDR3 comprises the amino acid sequence QQRSKYPPWT (SEQ ID NO: 48). In certain embodiments, the CDRs are according to the Kabat definition. In certain embodiments, the CDRs are according to the Chothia definition. In certain embodiments, the CDRs are according to the IMGT definition. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 3; and wherein the immunoglobulin light chain variable region comprises an amino acid sequence at least about 90%, 95%, 97%, 99%, or 100% identical to that set forth in SEQ ID NO: 4. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 5; and wherein the immunoglobulin light chain variable region comprises an amino acid sequence at least about 90%, 95%, 97%, 99%, or 100% identical to that set forth in SEQ ID NO: 6. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 7; and wherein the immunoglobulin light chain variable region comprises an amino acid sequence at least about 90%, 95%, 97%, 99%, or 100% identical to that set forth in SEQ ID NO: 8. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 9; and wherein the immunoglobulin light chain variable region comprises an amino acid sequence at least about 90%, 95%, 97%, 99%, or 100% identical to that set forth in SEQ ID NO: 10. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 11; and wherein the immunoglobulin light chain variable region comprises an amino acid sequence at least about 90%, 95%, 97%, 99%, or 100% identical to that set forth in SEQ ID NO: 12. In certain embodiments, the antibody or antigen binding fragment thereof comprises an immunoglobulin heavy chain variable region and an immunoglobulin light chain variable region, wherein the immunoglobulin heavy chain comprises an amino acid sequence at least about 90%, 95%, 97%, 99%, or 100% identical to that set forth in SEQ ID NO: 13; and wherein the immunoglobulin light chain variable region comprises an amino acid sequence at least about 90%, 95%, 97%, 99%, or 100% identical to that set forth in SEQ ID NO: 14. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 15; and wherein the immunoglobulin light chain variable region comprises an amino acid sequence at least about 90%, 95%, 97%, 99%, or 100% identical to that set forth in SEQ ID NO: 16. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 17; and wherein the immunoglobulin light chain variable region comprises an amino acid sequence at least about 90%, 95%, 97%, 99%, or 100% identical to that set forth in SEQ ID NO: 18. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 19; and wherein the immunoglobulin light chain variable region comprises an amino acid sequence at least about 90%, 95%, 97%, 99%, or 100% identical to that set forth in SEQ ID NO: 20. In certain embodiments, the antibody or antigen binding fragment thereof comprises an immunoglobulin heavy chain variable region and an immunoglobulin light chain variable region, wherein the immunoglobulin heavy chain variable region comprises an amino acid sequence at least about 90%, 95%, 97%, 99%, or 100% identical to that set forth in SEQ ID NO: 21; and wherein the immunoglobulin light chain variable region comprises an amino acid sequence at least about 90%, 95%, 97%, 99%, or 100% identical to that set forth in SEQ ID NO: 22. In certain embodiments, the antibody or antigen binding fragment thereof is an IgG antibody. In certain embodiments, the antibody or antigen binding fragment thereof is a Fab, $F(ab)_2$, or a single chain variable fragment (scFv). In certain embodiments, the antibody or antigen binding fragment thereof is chimeric or humanized. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 51; and wherein the immunoglobulin light chain comprises an amino acid sequence at least about 90%, 95%, 97%, 99%, or 100% identical to that set forth in SEQ ID NO: 52. In certain embodiments, the antibody possess a half-life of 14 days or longer in a human. In certain embodiments, the antibody possess a half-life of 21 days or longer in a human. In certain embodiments, the antibody possess a half-life of 25 days or longer in a human. In certain embodiments, the antibody possess a half-life of 30 days or longer in a human. In certain embodiments, the antibody or antigen binding fragment thereof comprises a M252Y/S254T/T256E substitution according to EU numbering in one or both heavy chain constant regions. In certain embodiments, the antibody inhibits signaling through IGF1R. In certain embodiments, the antibody possesses a $K_D$ of less than $5\times10^{-9}$ M. In certain embodiments, certain embodiments, the antibody possesses a $K_D$ of less than $1\times10^{-9}$ M. In certain embodiments, the antibody possesses a $K_D$ of less than $5\times10^{-10}$ M. Also described herein is a nucleic acid encoding the antibody or antigen binding fragment. Also described herein is a cell line comprising the nucleic acid encoding the antibody or antigen binding fragment thereof. In certain embodiments, the cell line is a Chinese Hamster Ovary cell line. Also described herein is a pharmaceutical composition comprising the antibody or antigen binding fragment thereof and a pharmaceutically acceptable excipient, carrier, or diluent. In certain embodiments, the pharmaceutical composition is formulated for intravenous administration. In certain embodiments, the pharmaceutical composition is formulated for subcutaneous administration. In certain embodiments, the antibody or antigen binding fragment thereof or the pharmaceutical composition is for use in method of inhibiting IGF1R signaling in an individual.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 1A illustrates multiple sequence alignment of heavy chain variable regions described herein. FIG. 1A discloses SEQ ID NOS 5, 3, 13, 11, 1, 1, 21, 9, 15, 19, and 17, respectively, in order of appearance.

FIG. 1B illustrates multiple sequence alignment of light chain variable regions described herein. FIG. 1B discloses SEQ ID NOS 22, 20, 18, 2, 4, 4, 4, 4, 4, 4, and 4, respectively, in order of appearance.

DETAILED DESCRIPTION

Figure 2:
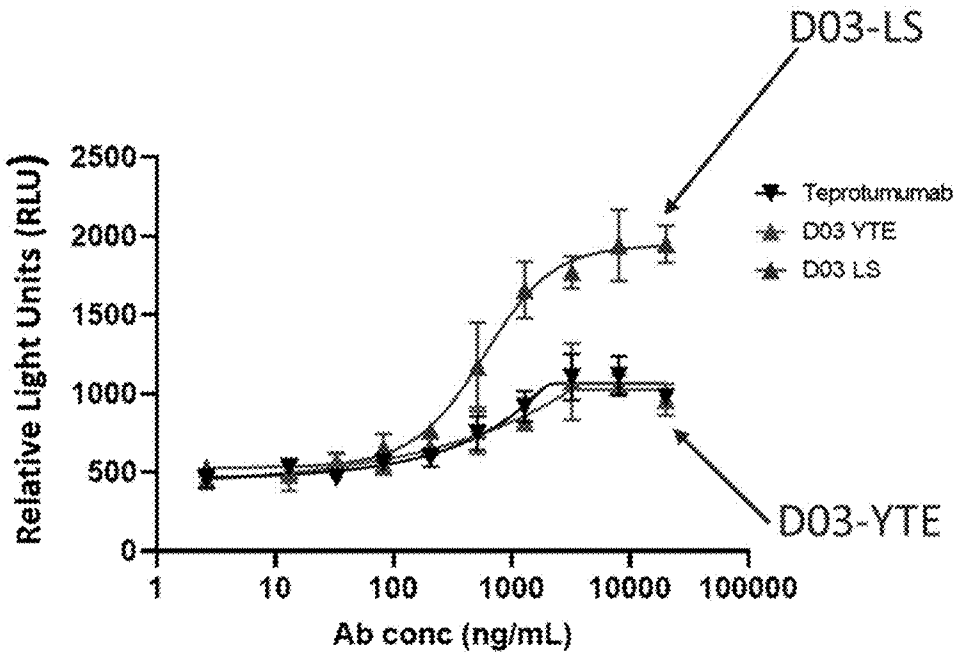
FIG. 2 illustrates an antibody dependent cell cytotoxicity (ADCC) assay performed with clone D03 formatted with different heavy chain constant regions (the "YTE" mutation, which possesses mutations at M252Y/S254T/T256E according to EU numbering; and the "LS" mutation Met428Leu/Asn434Ser according to EU numbering). RLU=Relative light units.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by 10% or less.

As used herein the term "individual," "patient," or "subject" refers to individuals diagnosed with, suspected of being afflicted with, or at-risk of developing at least one disease for which the described compositions and method are useful for treating. In certain embodiments the individual is a mammal. In certain embodiments, the mammal is a mouse, rat, rabbit, dog, cat, horse, cow, sheep, pig, goat, llama, alpaca, or yak. In certain embodiments, the individual is a human.

Among the provided antibodies are monoclonal antibodies, multispecific antibodies (for example, bispecific antibodies and polyreactive antibodies), and antibody fragments. The antibodies include antibody-conjugates and molecules comprising the antibodies, such as chimeric molecules. Thus, an antibody includes, but is not limited to, full-length and native antibodies, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, $F(ab')_2$, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. The monoclonal antibody can comprise a human IgG1 constant region. The monoclonal antibody can comprise a human IgG4 constant region.

The term "antibody" herein is used in the broadest sense and includes monoclonal antibodies, and includes intact antibodies and functional (antigen-binding) antibody fragments thereof, including fragment antigen binding (Fab) fragments, $F(ab')_2$ fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology,* 6th ed., W.H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

Specific binding or binding of antibody molecules described herein refers to binding mediated by one or more CDR portions of the antibody. Not all CDRs may be required for specific binding. Specific binding can be demonstrated for example by an ELISA against a specific recited target or antigen that shows significant increase in binding compared to an isotype control antibody.

As described herein an "epitope" refers to the binding determinant of an antibody or fragment described herein minimally necessary for specific binding of the antibody or fragment thereof to a target antigen. When the target antigen is a polypeptide the epitope will be a continuous or discontinuous epitope. A continuous epitope is formed by one region of the target antigen, while a discontinuous epitope may be formed from two or more separate regions. A discontinuous epitope, for example, may form when a target antigen adopts a tertiary structure that brings two amino acid sequences together and forms a three-dimensional structure bound by the antibody. When the target antigen is a polypeptide the epitope will generally be a plurality of amino acids linked into a polypeptide chain. A continuous epitope may comprise 5, 6, 7, 8, 9, 10, 11, 12, 13, 14, 15, 16, 17, 18, 19, or 20 contiguous amino acids. While an epitope may comprise a contiguous polymer of amino acids, not every amino acid of the polymer may be contacted by an amino acid residue of the antibody. Such non-contacted amino acids will still comprise part of the epitope as they may be important for the structure and linkage of the contacted amino acids. The skilled artisan may determine if any given antibody binds an epitope of a reference antibody, for example, by cross-blocking experiments with a reference antibody. In certain embodiments, described herein, are antibodies that bind the same epitope of the described antibodies. In certain embodiments, described herein, are antibodies that are competitively blocked by the described antibodies. In certain embodiments, described herein, are antibodies that compete for binding with the described antibodies.

Among the provided antibodies are antibody fragments. An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, $F(ab')_2$; diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., polypeptide linkers, and/or those that are not produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification" In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, an antibody provided herein has a dissociation constant ($K_D$) of about 1 μM, 100 nM, 50 nM, 40 nM, 30 nM, 20 nM, 10 nM, 5 nM, 2 nM, 1 nM, 0.5 nM, 0.1 nM, 0.05 nM, 0.01 nM or less (e.g., $10^{-8}$ M or less, e.g., from $10^{-8}$ M to $10^{-13}$ M, e.g., from $10^{-9}$ M to $10^{-13}$ M) for the antibody target. In some embodiments, an antibody provided herein has a dissociation constant ($K_D$) of about 100 nM, 50 nM, 40 nM, 30 nM, 20 nM, 10 nM, 5 nM, 2 nM, 1 nM, 0.5 nM, 0.1 nM, 0.05 nM, 0.01 nM, or 0.001 nM or greater (e.g., $10^{-8}$ M or less, e.g., from $10^{-8}$ M to $10^{-13}$ M, e.g., from $10^{-9}$ M to $10^{-13}$ M) for the antibody target. $K_D$ can be measured by any suitable assay. In certain embodiments, KD can be measured using surface plasmon resonance assays (e.g., using a BIACORE®-2000, a BIACORE®-3000 or Octet).

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some instances, the Fc region of an immunoglobulin is important for many important antibody functions (e.g. effector functions), such as antigen-dependent cellular cytotoxicity (ADCC), complement dependent cytotoxicity (CDC), and antibody-dependent cell-mediated phagocytosis (ADCP), result in killing of target cells, albeit by different mechanisms. Accordingly, in some embodiments, the antibodies described herein comprise the variable domains of the invention combined with constant domains comprising different Fc regions, selected based on the biological activities of the antibody for the intended use. In certain instances, Human IgGs, for example, can be classified into four subclasses, IgG1, IgG2, IgG3, and IgG4, and each these of these comprises an Fc region having a unique profile for binding to one or more of Fcγ receptors (activating receptors FcγRI (CD64), FcγRIIA, FcγRIIC (CD32); FcγRIIIA and FcγRIIIB (CD16) and inhibiting receptor FcγRIIB), and for the first component of complement (C1q). Human IgG1 and IgG3 bind to all Fcγ receptors; IgG2 binds to $FcγRIIA_{H131}$, and with lower affinity to $FcγRIIA_{R131}$ $FcγRIIIA_{V158}$; IgG4 binds to FcγRI, FcγRIIA, FcγRIIB, FcγRIIC, and $FcγRIIIA_{V158}$; and the inhibitory receptor FcγRIIB has a lower affinity for IgG1, IgG2 and IgG3 than all other Fcγ receptors. Studies have shown that FcγRI does not bind to IgG2, and FcγRIIIB does not bind to IgG2 or IgG4. Id. In general, with regard to ADCC activity, human IgG1≥IgG3>>IgG4≥IgG2.

In some embodiments, the antibodies of this disclosure are variants that possess reduced effector functions, which make it a desirable candidate for applications in which certain effector functions (such as complement fixation and ADCC) are unnecessary or deleterious. Such antibodies can have decreased complement-dependent cytotoxicity (CDC), antibody-dependent cell cytotoxicity (ADCC), or antibody dependent cellular phagocytosis (ADCP). In some embodiments, the antibodies of this disclosure are variants that possess increased effector functions for applications in which increased immunogenicity would be beneficial. Such antibodies can have increased CDC, ADCC, or ADCP, or a combination thereof. Non-limiting examples of in vitro assays to assess ADCC activity of a molecule of interest is described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

Antibodies can have increased half-lives and improved binding to the neonatal Fc receptor (FcRn) (See e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See e.g., U.S. Pat. No. 7,371,826). Other examples of Fc region variants are also contemplated (See e.g., Duncan & Winter, *Nature* 322:738-40 (1988); U.S. Pat. Nos. 5,648,260 and 5,624,821; and WO94/29351). One such mutation that confers increased half-life is the "YTE" mutation, which possesses mutations at M252Y/S254T/T256E according to EU numbering. Another such mutation that confers increased half-life is the "LS" mutation, which possesses mutations at Met428Leu/Asn434Ser according to EU numbering.

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region.

In some embodiments, an antibody provided herein may be further modified to contain additional nonproteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone)polyethylene glycol, polypropylene glycol homopolymers, polypropylen oxide/ethylene oxide co-polymers, polyoxyethylated polyols (e.g., glycerol), polyvinyl alcohol, and mixtures thereof. Polyethylene glycol propionaldehyde may have advantages in manufacturing due toits stability in water. The polymer may be of any molecular weight, and may be branched or unbranched. The number of polymers attached to the antibody may vary, and if two or more polymers are attached, they can be the same or different molecules.

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a genomic region. In certain embodiments, the expression vector is a plasmid. In certain embodiments, the expression vector is a lentivirus, adenovirus, or adeno-associated virus. In certain embodiments, the expression vector is an adenovirus. In certain embodiments, the expression vector is an adeno-associated virus. In certain embodiments, the expression vector is a lentivirus.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad.

Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large scale cell culture are known in the art. See e.g., Li et al., "Cell culture processes for monoclonal antibody production." *Mabs.* 2010 September-October; 2(5): 466-477. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NS0 murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

In certain embodiments, described herein, is a master cell bank comprising: (a) a mammalian cell line comprising a nucleic acid encoding an antibody described herein integrated at a genomic location; and (b) a cryoprotectant. In certain embodiments, the cryoprotectant comprises glycerol or DMSO. In certain embodiments, the master cell bank is contained in a suitable vial or container able to withstand freezing by liquid nitrogen.

Also described herein are methods of making an antibody described herein. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

"Treat," "treatment," or "treating," as used herein refers to, e.g., a deliberate intervention to a physiological disease state resulting in the reduction in severity of a disease or condition; the reduction in the duration of a condition course; the amelioration or elimination of one or more symptoms associated with a disease or condition; or the provision of beneficial effects to a subject with a disease or condition. Treatment does not require curing the underlying disease or condition.

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "pharmaceutically acceptable" with reference to a carrier" "excipient" or "diluent" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). Depending on the route of administration, the active compound, i.e., antibody, can be coated in a material to protect the compound from the action of acids and other natural conditions that can inactivate the compound.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Described herein in one aspect is an antibody or antigen binding fragment thereof that binds insulin like growth factor 1 receptor (IGF1R), wherein the antibody or antigen binding fragment thereof comprises: an immunoglobulin heavy chain CDR1 (HCDR1) comprising the amino acid sequence of any one of SEQ ID NOs: 30 to 33; an immunoglobulin heavy chain CDR2 (HCDR2) comprising the amino acid sequence of any one of SEQ ID NOs: 34 to 40; an immunoglobulin heavy chain CDR3 (HCDR3) comprising the amino acid sequence of any one of SEQ ID NOs: 41 or 42; an immunoglobulin light chain CDR1 (LCDR1) comprising the amino acid sequence of any one of SEQ ID NOs: 43 to 45; an immunoglobulin light chain CDR2 (LCDR2) comprising the amino acid sequence of SEQ ID NO: 46; and/or an immunoglobulin light chain CDR3 (LCDR3) comprising the amino acid sequence of any one of SEQ ID NOs: 47 to 49; wherein the antibody or antigen binding fragment thereof does not comprise an immunoglobulin heavy chain variable region identical to SEQ ID NO: 1 and/or an immunoglobulin light chain variable region identical to SEQ ID NO: 2.

Described herein in one aspect is an antibody or antigen binding fragment thereof that binds insulin like growth factor 1 receptor (IGF1R), wherein the antibody or antigen binding fragment thereof comprises: (a) an immunoglobulin heavy chain CDR1 (HCDR1) comprising the amino acid sequence $SX_1GMH$ (SEQ ID NO: 53), wherein $X_1$ is H, Y, A, or T; (b) an immunoglobulin heavy chain CDR2 (HCDR2) comprising the amino acid sequence $X_1IX_2X_3DX_4SX_5TYYADSVRG$ (SEQ ID NO: 54), wherein $X_1$ is I, T, or Y, $X_2$ is W, N, or A, $X_3$ is F, H, A, or G, $X_4$ is G or A, $X_5$ is S or T; (c) an immunoglobulin heavy chain CDR3 (HCDR3) comprising the amino acid sequence $ELX_1RRYFDL$ (SEQ ID NO: 55), wherein $X_1$ is G or N; (d) an immunoglobulin light chain CDR1 (LCDR1) comprising the amino acid sequence $RASQSVSSX_1LA$ (SEQ ID NO: 56), wherein $X_1$ is Y, A, or T; (e) an immunoglobulin light chain CDR2 (LCDR2) comprising the amino acid sequence DASKRAT (SEQ ID NO: 46); and/or an immunoglobulin light chain CDR3 (LCDR3) comprising the amino acid sequence $QQRX_1KX_2PPWT$ (SEQ ID NO: 57), wherein $X_1$ is S or G, $X_2$ is Y or W; wherein the antibody or antigen binding fragment thereof does not comprise an immunoglobulin heavy chain variable region identical to SEQ ID NO: 1 and/or an immunoglobulin light chain variable region identical to SEQ ID NO: 2. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 3; and wherein the immunoglobulin light chain comprises an amino acid sequence at least about 90%, 95%, 97%, 99%, or 100% identical to that set forth in SEQ ID NO: 4. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 5; and wherein the immunoglobulin light chain comprises an amino acid sequence at least about 90%, 95%, 97%, 99%, or 100% identical to that set forth in SEQ ID NO: 6. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 7; and wherein the immunoglobulin light chain comprises an amino acid sequence at least about 90%, 95%, 97%, 99%, or 100% identical to that set forth in SEQ ID NO: 8. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 9; and wherein the immunoglobulin light chain comprises an amino acid sequence at least about 90%, 95%, 97%, 99%, or 100% identical to that set forth in SEQ ID NO: 10. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 11; and wherein the immunoglobulin light chain comprises an amino acid sequence at least about 90%, 95%, 97%, 99%, or 100% identical to that set forth in SEQ ID NO: 12. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 13; and wherein the immunoglobulin light chain comprises an amino acid sequence at least about 90%, 95%, 97%, 99%, or 100% identical to that set forth in SEQ ID NO: 14. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 15; and wherein the immunoglobulin light chain comprises an amino acid sequence at least about 90%, 95%, 97%, 99%, or 100% identical to that set forth in SEQ ID NO: 16. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 17; and wherein the immunoglobulin light chain comprises an amino acid sequence at least about 90%, 95%, 97%, 99%, or 100% identical to that set forth in SEQ ID NO: 18. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 19; and wherein the immunoglobulin light chain comprises an amino acid sequence at least about 90%, 95%, 97%, 99%, or 100% identical to that set forth in SEQ ID NO: 20. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 21; and wherein the immunoglobulin light chain comprises an amino acid sequence at least about 90%, 95%, 97%, 99%, or 100% identical to that set forth in SEQ ID NO: 22. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 51; and wherein the immunoglobulin light chain comprises an amino acid sequence at least about 90%, 95%, 97%, 99%, or 100% identical to that set forth in SEQ ID NO: 52. In certain embodiments, the antibody or antigen binding fragment thereof is an IgG antibody. In certain embodiments, the antibody or antigen binding fragment thereof is a Fab, $F(ab)_2$, or a single chain variable fragment (scFv). In certain embodiments, the antibody or antigen binding fragment thereof is chimeric or humanized. In certain embodiments, the antibody inhibits signaling through IGF1R. In certain embodiments, the antibody possesses a $K_D$ of less than $5\times10^{-9}$ M. In certain embodiments, certain embodiments, the antibody possesses a $K_D$ of less than $1\times10^{-9}$ M. In certain embodiments, the antibody possesses a $K_D$ of less than $5\times10^{-10}$ M. In certain embodiments, the antibody possess a half-life of 14 days or longer in a human. In certain embodiments, the antibody possess a half-life of 21 days or longer in a human. In certain embodiments, the antibody comprise a M252Y/S254T/T256E substitution according to EU numbering in one or both heavy chain constant regions.

Described herein in one aspect is an antibody or antigen binding fragment thereof that binds insulin like growth factor 1 receptor (IGF1R), wherein the antibody or antigen binding fragment thereof comprises: (a) an HCDR1 comprising the amino acid sequence SHGMH (SEQ ID NO: 30); (b) an HCDR2 comprising the amino acid sequence YIWFDGSSTYYADSVRG (SEQ ID NO: 35); (c) an HCDR3 comprising the amino acid sequence ELGRRYFDL (SEQ ID NO: 41); (d) an LCDR1 comprising the amino acid sequence RASQSVSSALA (SEQ ID NO: 43); (e) an LCDR2 comprising the amino acid sequence DASKRAT (SEQ ID NO: 46); and/or (f) an LCDR3 comprising the amino acid sequence QQRSKYPPWT (SEQ ID NO: 48). In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 17; and wherein the immunoglobulin light chain comprises an amino acid sequence at least about 90%, 95%, 97%, 99%, or 100% identical to that set forth in SEQ ID NO: 18. In certain embodiments, the antibody or antigen binding fragment thereof comprises an immunoglobulin heavy chain and an immunoglobulin light chain, wherein the immunoglobulin heavy chain comprises an amino acid sequence identical to that set forth in SEQ ID NO: 17; and wherein the immunoglobulin light chain comprises an amino acid sequence identical to that set forth in SEQ ID NO: 18. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 51; and wherein the immunoglobulin light chain comprises an amino acid sequence at least about 90%, 95%, 97%, 99%, or 100% identical to that set forth in SEQ ID NO: 52. In certain embodiments, the antibody or antigen binding fragment thereof is an IgG antibody. In certain embodiments, the antibody or antigen binding fragment thereof is a Fab, $F(ab)_2$, or a single chain variable fragment (scFv). In certain embodiments, the antibody or antigen binding fragment thereof is chimeric or humanized. In certain embodiments, the antibody inhibits signaling through IGF1R. In certain embodiments, the antibody possesses a $K_D$ of less than $5\times10^{-9}$ M. In certain embodiments, certain embodiments, the antibody possesses a $K_D$ of less than $1\times10^{-9}$ M. In certain embodiments, the antibody possesses a $K_D$ of less than $5\times10^{-10}$ M. In certain embodiments, the antibody possess a half-life of 14 days or longer in a human. In certain embodiments, the antibody possess a half-life of 21 days or longer in a human. In certain embodiments, the antibody comprise a M252Y/S254T/T256E substitution according to EU numbering in one or both heavy chain constant regions.

Described herein in one aspect is an antibody or antigen binding fragment thereof that binds insulin like growth factor 1 receptor (IGF1R), wherein the antibody or antigen binding fragment thereof comprises: (a) an HCDR1 comprising the amino acid sequence SYGMH (SEQ ID NO: 33); (b) an HCDR2 comprising the amino acid sequence IIWFDGSSTYYADSVRG (SEQ ID NO: 38); (c) an HCDR3 comprising the amino acid sequence ELGRRYFDL (SEQ ID NO: 41); (d) an LCDR1 comprising the amino acid sequence RASQSVSSYLA (SEQ ID NO: 45); (e) an LCDR2 comprising the amino acid sequence DASKRAT (SEQ ID NO: 46); and/or (f)_an LCDR3 comprising the amino acid sequence QQRSKYPPWT (SEQ ID NO: 48). In certain embodiments, the antibody or antigen binding fragment thereof is an IgG antibody. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 7; and wherein the immunoglobulin light chain comprises an amino acid sequence at least about 90%, 95%, 97%, 99%, or 100% identical to that set forth in SEQ ID NO: 8. In certain embodiments, the antibody or antigen binding fragment thereof comprises an immunoglobulin heavy chain and an immunoglobulin light chain, wherein the immunoglobulin heavy chain comprises an amino acid sequence identical to that set forth in SEQ ID NO: 7; and wherein the immunoglobulin light chain comprises an amino acid sequence identical to that set forth in SEQ ID NO: 8. In certain embodiments, the antibody or antigen binding fragment thereof is a Fab, $F(ab)_2$, or a single chain variable fragment (scFv). In certain embodiments, the antibody or antigen binding fragment thereof is chimeric or humanized. In certain embodiments, the antibody inhibits signaling through IGF1R. In certain embodiments, the antibody possesses a $K_D$ of less than $5\times10^{-9}$ M. In certain embodiments, certain embodiments, the antibody possesses a $K_D$ of less than $1\times10^{-9}$ M. In certain embodiments, the antibody possesses a $K_D$ of less than $5\times10^{-10}$ M. In certain embodiments, the antibody possess a half-life of 14 days or longer in a human. In certain embodiments, the antibody possess a half-life of 21 days or longer in a human. In certain embodiments, the antibody comprise a M252Y/S254T/T256E substitution according to EU numbering in one or both heavy chain constant regions.

Described herein in one aspect is an antibody or antigen binding fragment thereof that binds insulin like growth factor 1 receptor (IGF1R), wherein the antibody or antigen binding fragment thereof comprises: (a) an HCDR1 comprising the amino acid sequence SHGMH (SEQ ID NO: 30); (b) an HCDR2 comprising the amino acid sequence IIAGDASTTYYADSVRG (SEQ ID NO: 34); (c) an HCDR3 comprising the amino acid sequence ELGRRYFDL (SEQ ID NO: 41); (d) an LCDR1 comprising the amino acid sequence RASQSVSSYLA (SEQ ID NO: 45); (e) an LCDR2 comprising the amino acid sequence DASKRAT (SEQ ID NO: 46); and/or (f) an LCDR3 comprising the amino acid sequence QQRSKYPPWT (SEQ ID NO: 48). In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 5; and wherein the immunoglobulin light chain comprises an amino acid sequence at least about 90%, 95%, 97%, 99%, or 100% identical to that set forth in SEQ ID NO: 6. In certain embodiments, the antibody or antigen binding fragment thereof comprises an immunoglobulin heavy chain and an immunoglobulin light chain, wherein the immunoglobulin heavy chain comprises an amino acid sequence identical to that set forth in SEQ ID NO: 5; and wherein the immunoglobulin light chain comprises an amino acid sequence identical to that set forth in SEQ ID NO: 6. In certain embodiments, the antibody or antigen binding fragment thereof is an IgG antibody. In certain embodiments, the antibody or antigen binding fragment thereof is a Fab, $F(ab)_2$, or a single chain variable fragment (scFv). In certain embodiments, the antibody or antigen binding fragment thereof is chimeric or humanized. In certain embodiments, the antibody inhibits signaling through IGF1R. In certain embodiments, the antibody possesses a $K_D$ of less than $5\times10^{-9}$ M. In certain embodiments, certain embodiments, the antibody possesses a $K_D$ of less than $1\times10^{-9}$ M. In certain embodiments, the antibody possesses a $K_D$ of less than $5\times10^{-10}$ M. In certain embodiments, the antibody possess a half-life of 14 days or longer in a human. In certain embodiments, the antibody possess a half-life of 21 days or longer in a human. In certain embodiments, the antibody possess a half-life of 25 days or longer in a human. In certain embodiments, the antibody possess a half-life of 30 days or longer in a human. In certain embodiments, the antibody comprise a M252Y/S254T/T256E substitution according to EU numbering in one or both heavy chain constant regions.

In one aspect, described herein, is a teprotumumab derivative with increased with increased affinity, wherein the teprotumumab derivative comprises a substitution of the tryptophan at position 94 of SEQ ID NO: 2 to tyrosine.

IGF1R signaling is perturbed (e.g., increased) in several diseases relevant to humans the antibodies described herein are potentially useful for the treatment of such diseases associated with this aberrant signaling. The antibodies described herein can be used to effectively treat individuals with IGF1R disorders by inhibiting IGF1R signaling. IGF1R signaling occurs primarily through the PI3K and the RAS pathways. IGF1R singling or inhibition of IGF1R signaling can be determined by phosphorylation of IGF1R. In certain embodiments, the antibodies described herein exhibit inhibition with an EC50 of 10 ng/mL or less. In certain embodiments, the antibodies described herein exhibit inhibition with an EC50 of 9 ng/mL or less. In certain embodiments, the antibodies described herein exhibit inhibition with an EC50 of 8 ng/mL or less. In certain embodiments, the antibodies described herein exhibit inhibition with an EC50 of 7 ng/mL or less. In certain embodiments, the antibodies described herein exhibit inhibition with an EC50 of 6 ng/mL or less. In certain embodiments, the antibodies described herein exhibit inhibition with an EC50 of 5 ng/mL or less. Such assays to determine EC50 are described herein and can be carried out with 200 ng/mL of recombinant human IGF-1 using 4×10^4 NCI-H322 cells/well in flat bottom 96-well plates.

In certain embodiments, the antibodies can be administered to a subject in need thereof (e.g., afflicted with an IGF1R signaling disorder or disease associated with aberrant IGF1R signaling) by any route suitable for the administration of antibody-containing pharmaceutical compositions, such as, for example, subcutaneous, intraperitoneal, intravenous, intramuscular, or intratumoral, etc. In certain embodiments, the antibodies are administered intravenously. In certain embodiments, the antibodies are administered subcutaneously. In certain embodiments, the antibodies are administered intratumoral. In certain embodiments, the antibodies are administered on a suitable dosage schedule, for example, weekly, twice weekly, monthly, twice monthly, once every two weeks, once every three weeks, or once a month etc. In certain embodiments, the antibodies are administered once every three weeks. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 1 mg/kg and about 20 mg/kg. In certain embodiments, the therapeutically acceptable amount is between about 1 mg/kg and about 10 mg/kg. In certain embodiments, the therapeutically acceptable amount is between about 5 mg/kg and about 30 mg/kg. In certain embodiments, the therapeutically acceptable amount is between about 5 mg/kg and about 20 mg/kg.

Pharmaceutically Acceptable Excipients, Carriers, and Diluents

In certain embodiments the anti-IGF1R antibodies of the current disclosure are included in a pharmaceutical composition comprising one or more pharmaceutically acceptable excipients, carriers, and diluents. Pharmaceutically acceptable excipients, carriers and diluents can be included to increase shelf-life, stability, or the administrability of the antibody. Such compounds include salts, pH buffers, detergents, anti-coagulants, and preservatives. In certain embodiments, the antibodies of the current disclosure are administered suspended in a sterile solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

Antibodies in formulations for subcutaneous administration are generally present in highly concentrated form comprising greater than 50 mg/ml, 100 mg/ml, 200 mg/ml, or 300 mg/ml. Many excipients useful for subcutaneous formulations are known. See. e.g., Wang et al., Antibody Therapeutics, 2021, Vol. 4, No. 4 262-273

In certain embodiments, the antibodies of the current disclosure can be shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than 7.0. In certain embodiments, the pH can be between 4.5 and 7.0, 4.5 and 6.5, 4.5 and 6.0, 4.5 and 5.5, 4.5 and 5.0, or 5.0 and 6.0.

Also described herein are kits comprising one or more of the antibodies described herein in a suitable container and one or more additional components selected from: instructions for use; a diluent, an excipient, a carrier, and a device for administration (e.g., a syringe/needle or other injector).

In certain embodiments, described herein is a method of preparing a composition for inhibiting IGF1R singling in an individual comprising admixing one or more pharmaceutically acceptable excipients, carriers, or diluents and an antibody of the current disclosure. In certain embodiments, described herein is a method of preparing a cancer treatment for storage or shipping comprising lyophilizing one or more antibodies of the current disclosure.

EXAMPLES

The following illustrative examples are representative of embodiments of compositions and methods described herein and are not meant to be limiting in any way.

Example 1—Determination of Antibody Affinity

In order to develop antibodies with higher affinities needed for a subcutaneous formulation multiple mutants of a reference antibody with teprotumumab variable regions (comprising variable regions comprising SEQ ID NO: 1 and SEQ ID NO 2) were tested to determine binding affinity. The antibodies described herein were tested for binding affinity to IGF1R by Octet. Results are shown below in Table 1. Sequence alignments of all teprotumumab mutants are shown in FIG. 1A and FIG. 1B. Surprisingly, mutation of the tryptophan at position 94 of the light chain to tyrosine was present in all antibodies. This was surprising as generally light chain CDRs are less important to binding affinity than heavy chain CDRs.

TABLE 1

| Antibody (Fab) | $K_D$ (M) | $k_{on}$ (1/Ms) | $k_{off}$ (1/s) |
|---|---|---|---|
| Reference (Teprotumumab) | 5.17E−09 | 1.51E+06 | 7.81E−03 |
| B10 | 8.98E−10 | 9.21E+05 | 8.26E−04 |
| B09 | 1.13E−09 | 7.05E+05 | 7.99E−04 |
| B02 | 1.54E−09 | 8.10E+05 | 1.25E−03 |
| D10 | 6.90E−10 | 9.84E+05 | 6.79E−04 |
| F02 | 1.92E−09 | 1.20E+06 | 2.30E−03 |
| H11 | 4.18E−10 | 1.78E+06 | 7.44E−04 |
| C10 | 4.47E−10 | 1.08E+06 | 4.85E−04 |
| D03 | 4.07E−10 | 1.48E+06 | 6.03E−04 |
| A11 | 8.49E−10 | 8.95E+05 | 7.60E−04 |
| E01 | 1.79E−10 | 2.66E+06 | 2.98E−04 |

Affinity Measurements of Teprotumumab Variants via Biolayer Inferometry

Human IGF-I R (Glu 31-Asn 932 with a polyhistidine tag at the C-terminus) expressed from human 293 cells (HEK293) was purchased from ACROBiosystems (Newark, DE). Dip and Read Ni-NTA (NTA) Biosensors from Sartorius (Bohemia, NY) pre-immobilized with nickel-charged Tris-NTA, were enabled for kinetic characterization of novel anti-human IGF-I R antibodies. Briefly, antibody variants were digested into purified Fab fragments (to enable 1:1 binding and global fitting). The FabALACTICA Fab kit from GENOVIS (Cambridge, MA) was used to generate a monovalent binding Fab domain of each antibody variant, Fab fragments are subsequently separated from Fc using the CaptureSelect™ Fc column. Binding of variant Fabs to NTA-captured human IGF-I R (His-tagged) was monitored by biolayer interferometry (BLI) on an Octet RED96e (Sartorius). NTA biosensors were charged with 10 mM NiCl2, then loaded with His-tagged human IGF-I R at approximately 5 ug/mL to an average loading response of 0.67 nm shift. Variant Fabs were assayed from 0-100 nM in 10× kinetics buffer (1×PBS, 0.1% BSA, 0.02% Tween-20 plus Kathon as a preservative) from Sartorius. Binding kinetics and affinities were determined using the Octet Analysis Studio Software (Sartorius) by applying a 1:1 global fitting to double-referenced subtracted data.

Example 2—Biological Activity of Teprotumumab Mutants

The biological activity of teprotumumab mutants was determined by assessing inhibition of IGF-1R phosphorylation and binding of ligands IGF-1 and IGF-2 to the receptor. Results are shown in Tables 2 to 4. Overall clones showed biological activity comparable to or better than the reference teprotumumab, indicating that improvements in affinity seen in example 2 extend to biological activity as well.

TABLE 2

| Inhibition of Phosphorylation | |
|---|---|
| | IC50 (ng/mL) |
| E01 | 6.4 |
| D03 | 4.9 |
| D10 | 6.7 |
| B09 | 8.3 |
| B10 | 16.2 |
| B02 | 13.5 |
| H11 | 21.1 |
| C10 | 6.5 |
| A11 | 11.5 |
| Teprotumumab reference | 10.6 |

TABLE 3

| IGF-1 inhibition | |
|---|---|
| | IC50 (ng/mL) |
| E01 | 387.5 |
| D03 | 387.8 |
| D10 | 386.3 |
| B09 | 336.8 |
| B10 | 394.5 |
| B02 | 385.5 |
| H11 | 452 |
| C10 | No data |
| A11 | 351.5 |
| Teprotumumab reference | 449 |

TABLE 4

| IGF-2 inhibition | |
|---|---|
| | IC50 (ng/mL) |
| E01 | 141.5 |
| D03 | 160.5 |
| D10 | 173.5 |
| B09 | 153.5 |
| B10 | 176.0 |
| B02 | 114.5 |
| H11 | 156.5 |
| C10 | No data |
| A11 | 157.5 |
| Teprotumumab reference | 260.3 |

Inhibition of IGF-1R Phosphorylation

4×10^4 NCI-H322 cells/well were seeded in flat bottom 96 well plate and incubated overnight in a 37° C., 5% incubator. Cells were treated with different concentration of anti-IGF1R for 1 hour and stimulated with 200 ng/mL of recombinant human IGF-1 protein for 30 minutes. Then, the phosphorylated IGF-1 in cell lysate was determined by Insulin Signaling Panel whole cell lysate kit (MSD) following manufactural protocol.

IGF-1 Inhibition of Binding Assay

Maxisorp plates were coated with 1.5 ug/mL of IGF-1R overnight at 4° C. Plates were washed and blocked with 1% BSA. Subsequently, serially diluted anti-IGF1R antibodies were incubated for 30 min at room temperature followed by an incubation with a final concentration of 20 ng/mL IGF-1 biotin. Plates were washed and streptavidin-horseradish peroxidase was added. After a final wash, 3,3',5,5'-Tetramethylbenzidine was added for 8 minutes. The reaction was terminated with a HCL based stop solution. Plates were measured for absorbance at 450 nM, and the data was analyzed using Softmax Pro 7.1 software.

IGF-2 Inhibition of Binding Assay

Maxisorp plates were coated with 1.5 ug/mL of IGF-1R overnight at 4° C. Plates were washed and blocked with 1% BSA. Subsequently, serially diluted anti-IGF1R antibodies were incubated for 30 min at room temperature followed by an incubation with a final concentration of 200 ng/mL of IGF-2 biotin. Plates were washed and streptavidin-horseradish peroxidase was added. After a final wash, 3,3',5,5'-Tetramethylbenzidine was added for 8 minutes. The reaction was terminated with a HCL based stop solution. Plates were measured for absorbance at 450 nM, and the data was analyzed using Softmax Pro 7.1 software.

Example 3—Clone D03 with YTE Mutation Shows ADCC Activity Comparable to Teprotumumab Higher affinity antibodies may promote greater antibody dependent cell cytotoxicity (ADCC) when administered to an individual. For use in treating ophthalmic conditions and other conditions associated with autoimmune or inflammatory conditions, an increase in ADCC would be undesirable. Clone D03 was selected for further testing of its ADCC activity using different heavy chain constant region mutations (the "YTE" mutation, which possesses mutations at M252Y/S254T/T256E according to EU numbering; and the "LS" mutation Met428Leu/Asn434Ser according to EU numbering). As shown in FIG. 2, compared to teprotumumab (inverted triangles), clone D03 formatted with an LS ("D03-LS") mutation surprisingly showed increased ADCC compared to clone D03 with the YTE mutation ("D03-YTE"). D03-YTE showed ADCC comparable to teprotumumab.

ADCC Assay

Antibodies were incubated with DU145 cells for 4 hours at the indicated concentration, at which time effector cells with a luminescent ADCC reporter were added for overnight incubation, BioGlo detection reagent was added for 10 minutes and results were read on a luminometer.

Example 3—Clone D03 with YTE Mutation Exhibits 2-3 Fold Increased Half-life Compared to Teprotumumab The half-life of clone D03-YTE was tested in cynomolgus monkeys. Cynomolgus monkeys were dosed with D03-YTE at 150 mg/kg IV, 150 mg/kg subcutaneous, or 75 mg/kg subcutaneous. Serum samples were collected at 2, 6, 24, 96, 168, 336, 504, 672, 1008, 1344, 1680, and 2016 hours. Serum samples were analyzed for D03-YTE by ELISA. As shown below in Table 5 D03 possesses a an increased serum half-life compared to teprotumumab.

TABLE 5

| Dose (mg/kg) | Route | $t_{1/2}$ (day)[1] | $AUC_{inf}$ (μg · day/mL) | $C_{max}$ (μg/mL) |
|---|---|---|---|---|
| 150 (n = 3) | IV | 29.9 (4.6) | 47980 (5941) | 3321 (489) |
| 150 (n = 2)[2] | SC | 22.4 | 27562 | 804 (33.0) |
| 75 (n = 5)[2] | SC | 18.6 (3.2) | 12905 (2001) | 412 (48.4) |
| Tepro (150) | IV | 10.1 | NA | NA |

Figure 3:
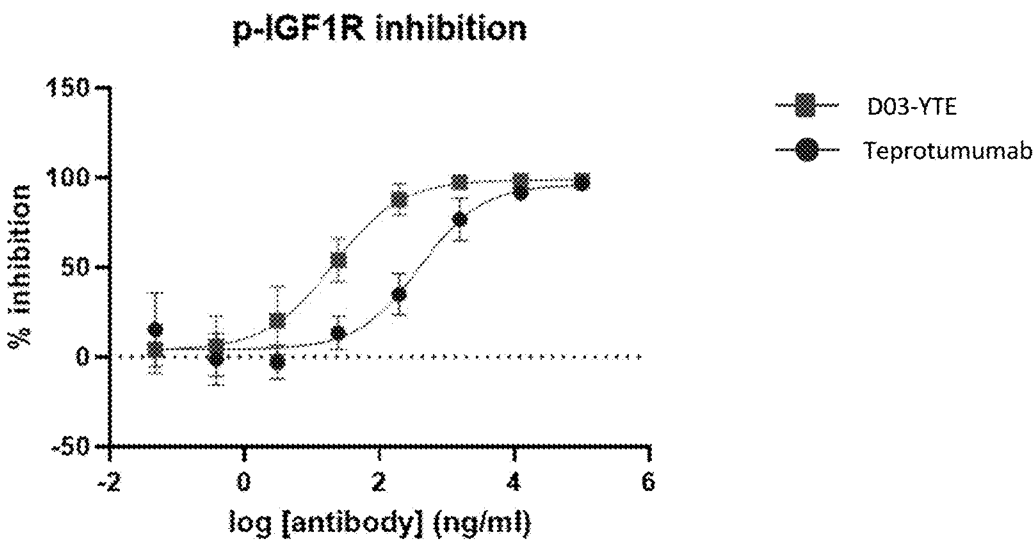
FIG. 3 illustrates inhibition of IGF-1R signaling by Teprotumumab and D03-YTE.

Example 4—Clone D03 with YTE Mutation Exhibits Increased Inhibition of IGF-1R Phosphorylation Compared to Teprotumumab D03-YTE was tested for its ability to inhibit IGF-1R phosphorylation. Experiments as described in Example 2 were conducted, with the following modification: dilution of anti-IGF-1R antibodies were started at 100 ug/mL and diluted ⅛ allowing 100% inhibition by teprotumumab. The experiments in FIG. 3 show that in this experimental set up Teprotumumab (circles) exhibited an IC50 of 397.4 ng/mL vs. 20.51 ng/mL for D03-YTE (squares).

Example 5—Teprotumumab Mutants Retain the Manufacturability of the Parent Clone One limiting factor when developing antibodies for subcutaneous injection, is that in addition to binding with high-affinity and/or possessing longer half-lives in vivo, the antibodies must possess favorable biophysical properties such as low hydrophobicity, propensity to form aggregates, and the ability to exist in formulations with a low viscosity. Any mutation made to antibody has the potential to negatively affect these characteristics, however as shown in this example despite increased affinity and biological potency there were no deleterious changes with respect to key manufacturability criteria. As shown in Table 6 D03 with a YTE mutation exhibited no increase in degradation when subjected to forced degradation at 40° C. for 28 days when compared to teprotumumab with a YTE mutation (Buffer composition: 20 mM Histidine/Histidine-HCl, 40 mM L-Methionine, 210 mM Trehalose, pH 5.5, 0.2% PX188).

TABLE 6

| | % Monomer loss/Month | | Fragmentation/Month | Aggregation/month* |
|---|---|---|---|---|
| | No exclusions | T0 Excluded | No exclusions | T0 Excluded |
| B09 LS | 0.4 | 0.52 | 0.52 | −0.16 |
| B09 YTE | 0.6 | 0.68 | 0.6 | 0 |
| D03 LS | 0.24 | 0.4 | 0.52 | −0.24 |
| D03 YTE | 0.4 | 0.4 | 0.52 | −0.16 |
| E01 LS | 0.4 | 0.52 | 0.52 | −0.12 |
| E01 YTE | 0.48 | 0.52 | 0.52 | 0 |
| Tepro LS | N.A. | 0.28 | 0.6 | −1.04 |
| Tepro WT | 0 | 0.4 | 0.56 | −0.56 |
| Tepro YTE | 0.32 | 0.52 | 0.64 | −0.24 |

Anti-IGF-1R variants were assessed to ensure that Fc and variable domain mutations did not significantly increase viscosity. See Table 7. Increased viscosity is undesirable as it may limit liquid formulation options for subcutaneous administration. Viscosity of the anti-IGF-1R variants were initially assessed at ~130 mg/ml. One variant (B09-YTE) exhibited increased viscosity compared to other variants and control mAbs and this variant was not assessed at higher concentrations. As there was little differentiation at ~130 mg/ml, viscosity was assessed at a higher concentration (~170 mg/ml). At 170 mg/ml all D03 and E01 variants had viscosity measurements below 20 cP and were similar to teprotumumab controls.

Antibodies were formulated in the following buffer: 20 mM Histidine/Histidine-HCl, 40 mM L-Methionine, 210 mM Trehalose, pH 5.5, 0.2% PX188. Antibodies were evaluated at 130 mg/ml & 170 mg/ml concentrations and at 20° & 25° C. Antibody concentration was determined via SoloVPE (in triplicate). Viscosity was assessed via a RheoSense m-VROC with the applying shear sweep rate 400-2700/s at 20° C. and 25° C. collecting 8-12 segments.

TABLE 7

| | Viscosity (cP) 135 mg/ml | | Viscosity (cP) 170 mg/ml | |
|---|---|---|---|---|
| | 20° C. | 25° C. | 20° C. | 25° C. |
| B09 LS | 8.1 | 6.9 | N.D. | N.D. |
| B09 YTE | 10.7 | 9.1 | N.D. | N.D. |
| D03 LS | 8 | 6.3 | 15.1 | 11 |
| D03 YTE | 8.4 | 6.6 | 12.7 | 9.3 |
| E01 LS | 7.8 | 6.5 | 12.8 | 10.5 |
| E01 YTE | 7.2 | 6 | 15.2 | 12.3 |
| Tepro LS | 7.2 | 6 | 13.9 | 11.2 |
| Tepro WT | 6.9 | 5.8 | 11.4* | 9.3* |
| Tepro YTE | 7.4 | 6.3 | N.D. | N.D. |

Anti-IGF-1R variants were assessed by Hydrophobic Interaction Chromatography (HIC) analysis (Table 8). HIC is an emerging assessment of the hydrophobic character of antibodies and other proteins. Too much hydrophobic character can be detrimental to overall stability and lead to increases in non-specific binding and self-interactions. All Anti-IGF-1R variants had elution profiles similar to teprotumumab controls. No increases in hydrophobic character were observed. Teprotumumab and its variants eluted earlier that the positive control (NISTmAb) and significantly earlier than CNTO607 (a mAb with known hydrophobic character causing developability issues). These data suggest the mutations introduced to increase either IGF-1R affinity or half-life extension did not affect the overall hydrophobic character of the variants.

HIC was performed using an Agilent 1260 Infinity II HPLC with a ProPac HIC-10, 5 μm, 4.6×100 mm column (ThermoFisher PN: 063655). Method parameters were taken directly from the MabPAC-10 product insert. The following buffers were used: BufferA: 2 M ammonium sulfate, 0.1 M sodium phosphate, 2-propanol (93:7 v/v), pH 7.0; BufferB: 0.1 M sodium phosphate, 2-propanol (93:7 v/v), pH 7.0. After 5 minutes equilibration in 95% Buffer A and 5% Buffer B, a 25-minute gradient ending with 100% buffer B was employed. The temperature was 30° C. and UV detection at 214 nM was used to visualize protein elution. NISTmAb (positive control human IgG1) and CNTO607 (a mAb with known hydrophobic character) were also evaluated as comparators.

TABLE 8

| | Retention Time (min) |
|---|---|
| B09 LS | 21.0 |
| B09 YTE | 20.9 |
| D03 LS | 21.2 |
| D03 YTE | 21.1 |
| E01 LS | 21.2 |
| E01 YTE | 21.0 |
| Tepro LS | 21.5 |
| Tepro WT | 21.3 |
| Tepro YTE | 21.4 |
| NISTmAb | 22.6 |
| CNTO607 | 25.7 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure. Sequences described herein

SEQ ID NO 1

```
>Teprotumumab_VH
QVELVESGGGVVQPGRSQRLSCAASGFTFSSYGMHWVRQAPGKGLEWVAIIWFDGSST
YYADSVRGRFTISRDNSKNTLYLQMNSLRAEDTAVYFCARELGRRYFDLWGRGTLVSV
SS
```

SEQ ID NO 2

```
>Teprotumumab_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKWPPWTFGQGTKVESK
```

SEQ ID NO 3

```
>B02_VH
QVELVESGGGVVQPGRSQRLSCAASGFTFSSTGMHWVRQAPGKGLEWVAYIWFDGSST
YYADSVRGRFTISRDNSKNTLYLQMNSLRAEDTAVYFCARELNRRYFDLWGRGTLVSV
SS
```

SEQ ID NO 4

```
>B02_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK
```

-continued

SEQ ID NO 5
>B09_VH
QVELVESGGGVVQPGRSQRLSCAASGFTFSSHGMHWVRQAPGKGLEWVAIIAGDASTT
YYADSVRGRFTISRDNSKNTLYLQMNSLRAEDTAVYFCARELGRRYFDLWGRGTLVSV
SS

SEQ ID NO 6
>B09_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK

SEQ ID NO 7
>E01_VH
QVELVESGGGVVQPGRSQRLSCAASGFTFSSYGMHWVRQAPGKGLEWVAIIWFDGSST
YYADSVRGRFTISRDNSKNTLYLQMNSLRAEDTAVYFCARELGRRYFDLWGRGTLVSV
SS

SEQ ID NO 8
>E01_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK

SEQ ID NO 9
>B10_VH
QVELVESGGGVVQPGRSQRLSCAASGFTFSSYGMHWVRQAPGKGLEWVATIWFDGSST
YYADSVRGRFTISRDNSKNTLYLQMNSLRAEDTAVYFCARELGRRYFDLWGRGTLVSV
SS

SEQ ID NO 10
>B10_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK

SEQ ID NO 11
>D10_VH
QVELVESGGGVVQPGRSQRLSCAASGFTFSSYGMHWVRQAPGKGLEWVAIINFDGSST
YYADSVRGRFTISRDNSKNTLYLQMNSLRAEDTAVYFCARELGRRYFDLWGRGTLVSV
SS

SEQ ID NO 12
>D10_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK

SEQ ID NO 13
>C10_VH
QVELVESGGGVVQPGRSQRLSCAASGFTFSSAGMHWVRQAPGKGLEWVAIIWADGSST
YYADSVRGRFTISRDNSKNTLYLQMNSLRAEDTAVYFCARELGRRYFDLWGRGTLVSV
SS

SEQ ID NO 14
>C10_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK

SEQ ID NO 15
>A11_VH
QVELVESGGGVVQPGRSQRLSCAASGFTFSSYGMHWVRQAPGKGLEWVAYIWFDGSST
YYADSVRGRFTISRDNSKNTLYLQMNSLRAEDTAVYFCARELGRRYFDLWGRGTLVSV
SS

SEQ ID NO 16
>A11_VL
EIVLTQSPATLSLSPGERATLSCRASQSVSSYLAWYQQKPGQAPRLLIYDASKRATGIPAR
FSGSGSGTDFTLTISSLEPEDFAVYYCQQRSKYPPWTFGQGTKVESK

SEQ ID NO 17
>D03_VH
QVELVESGGGVVQPGRSQRLSCAASGFTFSSHGMHWVRQAPGKGLEWVAYIWFDGSST
YYADSVRGRFTISRDNSKNTLYLQMNSLRAEDTAVYFCARELGRRYFDLWGRGTLVSV
SS

SEQ ID NO 18
>D03_VL
EIVLTQSPATLSLSPGERATLSCRASQSVSSALAWYQQKPGQAPRLLIYDASKRATGIPAR
FSGSGSGTDFTLTISSLEPEDFAVYYCQQRSKYPPWTFGQGTKVESK

SEQ ID NO 19
>F02_VH
QVELVESGGGVVQPGRSQRLSCAASGFTFSSHGMHWVRQAPGKGLEWVATIWFDGSST

-continued

YYADSVRGRFTISRDNSKNTLYLQMNSLRAEDTAVYFCARELGRRYFDLWGRGTLVSV
SS

SEQ ID NO 20

>F02_VL
EIVLTQSPATLSLSPGERATLSCRASQSVSSTLAWYQQKPGQAPRLLIYDASKRATGIPAR
FSGSGSGTDFTLTISSLEPEDFAVYYCQQRSKYPPWTFGQGTKVESK

SEQ ID NO 21

>H11_VH
QVELVESGGGVVQPGRSQRLSCAASGFTFSSYGMHWVRQAPGKGLEWVATIWHDGSS
TYYADSVRGRFTISRDNSKNTLYLQMNSLRAEDTAVYFCARELGRRYFDLWGRGTLVS
VSS

SEQ ID NO 22

>H11_VL
EIVLTQSPATLSLSPGERATLSCRASQSVSSALAWYQQKPGQAPRLLIYDASKRATGIPAR
FSGSGSGTDFTLTISSLEPEDFAVYYCQQRGKYPPWTFGQGTKVESK

| SEQ ID NO | | SEQUENCE |
|---|---|---|
| 30 | HCDR1 | SHGMH |
| 31 | HCDR1 | STGMH |
| 32 | HCDR1 | SAGMH |
| 33 | HCDR1 | SYGMH |
| 34 | HCDR2 | IIAGDASTTYYADSVRG |
| 35 | HCDR2 | YIWFDGSSTYYADSVRG |
| 36 | HCDR2 | IIWADGSSTYYADSVRG |
| 37 | HCDR2 | IINFDGSSTYYADSVRG |
| 38 | HCDR2 | IIWFDGSSTYYADSVRG |
| 39 | HCDR2 | TIWHDGSSTYYADSVRG |
| 40 | HCDR2 | TIWFDGSSTYYADSVRG |
| 41 | HCDR3 | ELGRRYFDL |
| 42 | HCDR3 | ELNRRYFDL |
| 43 | LCDR1 | RASQSVSSALA |
| 44 | LCDR1 | RASQSVSSTLA |
| 45 | LCDR1 | RASQSVSSYLA |
| 46 | LCDR2 | DASKRAT |
| 47 | LCDR3 | QQRGKYPPWT |
| 48 | LCDR3 | QQRSKYPPWT |
| 49 | LCDR3 | QQRSKWPPWT |
| 51 | Heavy chain | QVELVESGGGVVQPGRSQRLSCAASGFTFSSHGMHWVRQAPGK<br>GLEWVAYIWFDGSSTYYADSVRGRFTISRDNSKNTLYLQMNSLR<br>AEDTAVYFCARELGRRYFDLWGRGTLVSVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKKVEPKSC<br>DKTHTCPPCPAPELLGGPSVFLFPPKPKDTLYITREPEVTCVVVDV<br>SHEDPEVKFNWYVDGVEVHNAKTKPREEQYNSTYRVVSVLTVL<br>HQDWLNGKEYKCKVSNKALPAPIEKTISKAKGQPREPQVYTLPPS<br>RDELTKNQVSLTCLVKGFYPSDIAVEWESNGQPENNYKTTPPVL<br>DSDGSFFLYSKLTVDKSRWQQGNVFSCSVMHEALHNHYTQKSLS<br>LSPGK |
| 52 | Light chain | EIVLTQSPATLSLSPGERATLSCRASQSVSSALAWYQQKPGQAPR<br>LLIYDASKRATGIPARFSGSGSGTDFTLTISSLEPEDFAVYYCQQRS |

-continued

| SEQ ID NO | SEQUENCE |
|---|---|
| | KYPPWTFGQGTKVESKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGEC |

What is claimed is:

1. An antibody or antigen binding fragment thereof that binds insulin like growth factor 1 receptor (IGF1R), wherein the antibody or antigen binding fragment thereof comprises an immunoglobulin heavy chain variable region and an immunoglobulin light chain variable region, wherein the immunoglobulin heavy chain variable region comprises:

a. an immunoglobulin heavy chain CDR1 (HCDR1) comprising the amino acid sequence $SX_1GMH$, wherein $X_1$ is H, Y, A, or T;

b. an immunoglobulin heavy chain CDR2 (HCDR2) comprising the amino acid sequence $X_1IX_2X_3DX_4SX_5TYYADSVRG$, wherein $X_1$ is I, T, or Y, $X_2$ is W, N, or A, $X_3$ is F, H, A, or G, $X_4$ is G or A, $X_5$ is S or T; and c. an immunoglobulin heavy chain CDR3 (HCDR3) comprising the amino acid sequence $ELX_1RRYFDL$, wherein $X_1$ is G or N; and wherein the immunoglobulin light chain variable region comprises:

d. an immunoglobulin light chain CDR1 (LCDR1) comprising the amino acid sequence $RASQSVSSX_1LA$, wherein $X_1$ is Y, A, or T;

e. an immunoglobulin light chain CDR2 (LCDR2) comprising the amino acid sequence DASKRAT; and f. an immunoglobulin light chain CDR3 (LCDR3) comprising the amino acid sequence $QQRX_1KX_2PPWT$, wherein $X_1$ is S or G, $X_2$ is Y.

2. The antibody or antigen binding fragment thereof of claim 1, wherein:

a. the HCDR1 comprises the amino acid sequence of SEQ ID NO: 30 (SHGMH);

b. the HCDR2 comprises the amino acid sequence of SEQ ID NO: 35 (YIWFDGSSTYYADSVRG);

c. the HCDR3 comprises the amino acid sequence of SEQ ID NO: 41 (ELGRRYFDL);

d. the LCDR1 comprises the amino acid sequence of SEQ ID NO: 43 (RASQSVSSALA);

e. the LCDR2 comprises the amino acid sequence of SEQ ID NO: 46 (DASKRAT); and f. the LCDR3 comprises the amino acid sequence of SEQ ID NO: 48 (QQRSKYPPWT).

3. The antibody or antigen binding fragment thereof of claim 1, wherein:

a. the HCDR1 comprises the amino acid sequence of SEQ ID NO: 33 (SYGMH);

b. the HCDR2 comprises the amino acid sequence of SEQ ID NO: 38 (IIWFDGSSTYYADSVRG);

c. the HCDR3 comprises the amino acid sequence of SEQ ID NO: 41 (ELGRRYFDL);

d. the LCDR1 comprises the amino acid sequence of SEQ ID NO: 45 (RASQSVSSYLA);

e. the LCDR2 comprises the amino acid sequence of SEQ ID NO: 46 (DASKRAT); and f. the LCDR3 comprises the amino acid sequence of SEQ ID NO: 48 (QQRSKYPPWT).

4. The antibody or antigen binding fragment thereof of claim 1, wherein:

a. the HCDR1 comprises the amino acid sequence of SEQ ID NO: 30 (SHGMH);

b. the HCDR2 comprises the amino acid sequence of SEQ ID NO: 34 (IIAGDASTTYYADSVRG);

c. the HCDR3 comprises the amino acid sequence of SEQ ID NO: 41 (ELGRRYFDL);

d. the LCDR1 comprises the amino acid sequence of SEQ ID NO: 45 (RASQSVSSYLA);

e. the LCDR2 comprises the amino acid sequence of SEQ ID NO: 46 (DASKRAT); and f. the LCDR3 comprises the amino acid sequence of SEQ ID NO: 48 (QQRSKYPPWT).

5. The antibody or antigen binding fragment thereof of claim 1, wherein the immunoglobulin heavy chain variable region comprises the amino acid sequence set forth in SEQ ID NO: 3; and wherein the immunoglobulin light chain variable region comprises the amino acid sequence set forth in SEQ ID NO: 4.

6. The antibody or antigen binding fragment thereof of claim 1, wherein the immunoglobulin heavy chain variable region comprises the amino acid sequence set forth in SEQ ID NO: 5; and wherein the immunoglobulin light chain variable region comprises the amino acid sequence set forth in SEQ ID NO: 6.

7. The antibody or antigen binding fragment thereof of claim 1, wherein the immunoglobulin heavy chain variable region comprises the amino acid sequence set forth in SEQ ID NO: 7; and wherein the immunoglobulin light chain variable region comprises the amino acid sequence set forth in SEQ ID NO: 8.

8. The antibody or antigen binding fragment thereof of claim 1, wherein the immunoglobulin heavy chain variable region comprises the amino acid sequence set forth in SEQ ID NO: 9; and wherein the immunoglobulin light chain variable region comprises the amino acid sequence set forth in SEQ ID NO: 10.

9. The antibody or antigen binding fragment thereof of claim 1, wherein the immunoglobulin heavy chain variable region comprises the amino acid sequence set forth in SEQ ID NO: 11; and wherein the immunoglobulin light chain variable region comprises the amino acid sequence set forth in SEQ ID NO: 12.

10. The antibody or antigen binding fragment thereof of claim 1, wherein the immunoglobulin heavy chain variable region comprises the amino acid sequence set forth in SEQ ID NO: 13; and wherein the immunoglobulin light chain variable region comprises the amino acid sequence set forth in SEQ ID NO: 14.

11. The antibody or antigen binding fragment thereof of claim 1, wherein the immunoglobulin heavy chain variable region comprises the amino acid sequence set forth in SEQ ID NO: 15; and wherein the immunoglobulin light chain variable region comprises the amino acid sequence set forth in SEQ ID NO: 16.

12. The antibody or antigen binding fragment thereof of claim 1, wherein the immunoglobulin heavy chain variable region comprises the amino acid sequence set forth in SEQ ID NO: 17; and wherein the immunoglobulin light chain variable region comprises the amino acid sequence set forth in SEQ ID NO: 18.

13. The antibody or antigen binding fragment thereof of claim 1, wherein the immunoglobulin heavy chain variable region comprises the amino acid sequence set forth in SEQ ID NO: 19; and wherein the immunoglobulin light chain variable region comprises the amino acid sequence set forth in SEQ ID NO: 20.

14. The antibody or antigen binding fragment thereof of claim 1, wherein the immunoglobulin heavy chain variable region comprises the amino acid sequence set forth in SEQ ID NO: 21; and wherein the immunoglobulin light chain variable region comprises the amino acid sequence to that set forth in SEQ ID NO: 22.

15. The antibody or antigen binding fragment thereof of claim 1, wherein the antibody or antigen binding fragment thereof is an IgG antibody or antigen binding fragment thereof.

16. The antibody or antigen binding fragment thereof of claim 1, wherein the antigen binding fragment is a Fab, $F(ab)_2$, or a single chain variable fragment (scFv).

17. The antibody or antigen binding fragment thereof of claim 1, comprising an immunoglobulin heavy chain and an immunoglobulin light chain, wherein the immunoglobulin heavy chain comprises M252Y, S254T, and T256E substitutions according to EU numbering.

18. The antibody or antigen binding fragment thereof of claim 17, wherein the antibody or antigen binding fragment thereof is characterized by a half-life of 25 days or longer in a human.

19. The antibody or antigen binding fragment thereof of claim 1, wherein the antibody or antigen binding fragment thereof inhibits signaling through IGF1R.

20. The antibody or antigen binding fragment thereof of claim 1, wherein the antibody binds to human IGF1R with a $K_D$ of less than $5\times10^{-9}$ M.

21. A nucleic acid encoding an antibody or antigen binding fragment thereof that binds IGF1R, wherein the antibody or antigen binding fragment thereof comprises an immunoglobulin heavy chain variable region and an immunoglobulin light chain variable region, wherein the immunoglobulin heavy chain variable region comprises:

a. an immunoglobulin heavy chain CDR1 (HCDR1) comprising the amino acid sequence $SX_1GMH$, wherein $X_1$ is H, Y, A, or T;

b. an immunoglobulin heavy chain CDR2 (HCDR2) comprising the amino acid sequence $X_1IX_2X_3DX_4SX_5TYYADSVRG$, wherein $X_1$ is I, T, or Y, $X_2$ is W, N, or A, $X_3$ is F, H, A, or G, $X_4$ is G or A, $X_5$ is S or T; and c. an immunoglobulin heavy chain CDR3 (HCDR3) comprising the amino acid sequence $ELX_1RRYFDL$, wherein $X_1$ is G or N; and wherein the immunoglobulin light chain variable region comprises:

d. an immunoglobulin light chain CDR1 (LCDR1) comprising the amino acid sequence $RASQSVSSX_1LA$, wherein $X_1$ is Y, A, or T;

e. an immunoglobulin light chain CDR2 (LCDR2) comprising the amino acid sequence DASKRAT; and f. an immunoglobulin light chain CDR3 (LCDR3) comprising the amino acid sequence $QQRX_1KX_2PPWT$, wherein $X_1$ is S or G, $X_2$ is Y.

22. A cell line comprising the nucleic acid of claim 21.

23. The cell line of claim 22, wherein the cell line is a Chinese Hamster Ovary cell line.

24. A pharmaceutical composition comprising the antibody or antigen binding fragment thereof of claim 1 and a pharmaceutically acceptable excipient, carrier, or diluent.

25. The pharmaceutical composition of claim 24, formulated for intravenous administration.

26. The pharmaceutical composition of claim 24, formulated for subcutaneous administration.

27. A monoclonal antibody that binds IGF1R comprising an immunoglobulin heavy chain and an immunoglobulin light chain, wherein the immunoglobulin heavy chain comprises an immunoglobulin heavy chain variable region comprising:

an HCDR1 comprising the amino acid sequence of SEQ ID NO: 30 (SHGMH);

an HCDR2 comprising the amino acid sequence of SEQ ID NO: 35 (YIWFDGSSTYYADSVRG); and an HCDR3 comprising the amino acid sequence of SEQ ID NO: 41 (ELGRRYFDL); and wherein the immunoglobulin light chain comprises an immunoglobulin light chain variable region comprising:

a LCDR1 comprising the amino acid sequence of SEQ ID NO: 43 (RASQSVSSALA);

a LCDR2 comprising the amino acid sequence of SEQ ID NO: 46 (DASKRAT); and a LCDR3 comprising the amino acid sequence of SEQ ID NO: 48 (QQRSKYPPWT).

28. The monoclonal antibody of claim 27, wherein the immunoglobulin heavy chain variable region comprises the amino acid sequence of SEQ ID NO: 17 and the immunoglobulin light chain variable region comprises the amino acid sequence of SEQ ID NO: 18.

29. The monoclonal antibody of claim 27, wherein the immunoglobulin heavy chain comprises a human IgG1 constant region having M252Y, S254T, and T256E substitutions according to EU numbering.

30. The monoclonal antibody of claim 27, wherein the immunoglobulin heavy chain comprises the amino acid sequence of SEQ ID NO: 51 and the immunoglobulin light chain comprises the amino acid sequence of SEQ ID NO: 52.

31. A pharmaceutical composition comprising the monoclonal antibody of claim 27 and a pharmaceutically acceptable excipient, carrier, or diluent.

32. A pharmaceutical composition comprising the monoclonal antibody of claim 28 and a pharmaceutically acceptable excipient, carrier, or diluent.

33. A pharmaceutical composition comprising the monoclonal antibody of claim 30 and a pharmaceutically acceptable excipient, carrier, or diluent.

34. A nucleic acid encoding a monoclonal antibody that binds IGF1R, said monoclonal antibody comprising an immunoglobulin heavy chain and an immunoglobulin light chain, wherein the immunoglobulin heavy chain comprises an immunoglobulin heavy chain variable region comprising:

an HCDR1 comprising the amino acid sequence of SEQ ID NO: 30 (SHGMH);

an HCDR2 comprising the amino acid sequence of SEQ ID NO: 35 (YIWFDGSSTYYADSVRG); and an HCDR3 comprising the amino acid sequence of SEQ ID NO: 41 (ELGRRYFDL); and wherein the immunoglobulin light chain comprises an immunoglobulin light chain variable region comprising:

a LCDR1 comprising the amino acid sequence of SEQ ID NO: 43 (RASQSVSSALA);

a LCDR2 comprising the amino acid sequence of SEQ ID NO: 46 (DASKRAT); and a LCDR3 comprising the amino acid sequence of SEQ ID NO: 48 (QQRSKYPPWT).

35. The nucleic acid of claim 34, wherein the immunoglobulin heavy chain variable region comprises the amino acid sequence of SEQ ID NO: 17 and the immunoglobulin light chain variable region comprises the amino acid sequence of SEQ ID NO: 18.

36. The nucleic acid of claim 34, wherein the immunoglobulin heavy chain comprises the amino acid sequence of SEQ ID NO: 51 and the immunoglobulin light chain comprises the amino acid sequence of SEQ ID NO: 52.

37. A cell line comprising the nucleic acid of claim 34.

38. A cell line comprising the nucleic acid of claim 35.

39. A cell line comprising the nucleic acid of claim 36.

* * * * *

SEQUENCE LISTING

```
Sequence total quantity: 57
SEQ ID NO: 1            moltype = AA  length = 118
FEATURE                 Location/Qualifiers
source                  1..118
                        mol_type = protein
                        organism = synthetic construct
SEQUENCE: 1
QVELVESGGG VVQPGRSQRL SCAASGFTFS SYGMHWVRQA PGKGLEWVAI IWFDGSSTYY  60
ADSVRGRFTI SRDNSKNTLY LQMNSLRAED TAVYFCAREL GRRYFDLWGR GTLVSVSS    118

SEQ ID NO: 2            moltype = AA  length = 108
FEATURE                 Location/Qualifiers
source                  1..108
                        mol_type = protein
                        organism = synthetic construct
SEQUENCE: 2
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKWPPWTFG QGTKVESK               108

SEQ ID NO: 3            moltype = AA  length = 118
FEATURE                 Location/Qualifiers
source                  1..118
                        mol_type = protein
                        organism = synthetic construct
SEQUENCE: 3
QVELVESGGG VVQPGRSQRL SCAASGFTFS STGMHWVRQA PGKGLEWVAY IWFDGSSTYY  60
ADSVRGRFTI SRDNSKNTLY LQMNSLRAED TAVYFCAREL NRRYFDLWGR GTLVSVSS    118

SEQ ID NO: 4            moltype = AA  length = 108
FEATURE                 Location/Qualifiers
source                  1..108
                        mol_type = protein
                        organism = synthetic construct
SEQUENCE: 4
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK               108

SEQ ID NO: 5            moltype = AA  length = 118
FEATURE                 Location/Qualifiers
source                  1..118
                        mol_type = protein
                        organism = synthetic construct
SEQUENCE: 5
QVELVESGGG VVQPGRSQRL SCAASGFTFS SHGMHWVRQA PGKGLEWVAI IAGDASTTYY  60
ADSVRGRFTI SRDNSKNTLY LQMNSLRAED TAVYFCAREL GRRYFDLWGR GTLVSVSS    118

SEQ ID NO: 6            moltype = AA  length = 108
FEATURE                 Location/Qualifiers
source                  1..108
                        mol_type = protein
                        organism = synthetic construct
SEQUENCE: 6
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK               108

SEQ ID NO: 7            moltype = AA  length = 118
FEATURE                 Location/Qualifiers
source                  1..118
                        mol_type = protein
                        organism = synthetic construct
SEQUENCE: 7
QVELVESGGG VVQPGRSQRL SCAASGFTFS SYGMHWVRQA PGKGLEWVAI IWFDGSSTYY  60
ADSVRGRFTI SRDNSKNTLY LQMNSLRAED TAVYFCAREL GRRYFDLWGR GTLVSVSS    118

SEQ ID NO: 8            moltype = AA  length = 108
FEATURE                 Location/Qualifiers
```

-continued

```
source                  1..108
                        mol_type = protein
                        organism = synthetic construct
SEQUENCE: 8
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK              108

SEQ ID NO: 9            moltype = AA  length = 118
FEATURE                 Location/Qualifiers
source                  1..118
                        mol_type = protein
                        organism = synthetic construct
SEQUENCE: 9
QVELVESGGG VVQPGRSQRL SCAASGFTFS SYGMHWVRQA PGKGLEWVAT IWFDGSSTYY  60
ADSVRGRFTI SRDNSKNTLY LQMNSLRAED TAVYFCAREL GRRYFDLWGR GTLVSVSS    118

SEQ ID NO: 10           moltype = AA  length = 108
FEATURE                 Location/Qualifiers
source                  1..108
                        mol_type = protein
                        organism = synthetic construct
SEQUENCE: 10
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK              108

SEQ ID NO: 11           moltype = AA  length = 118
FEATURE                 Location/Qualifiers
source                  1..118
                        mol_type = protein
                        organism = synthetic construct
SEQUENCE: 11
QVELVESGGG VVQPGRSQRL SCAASGFTFS SYGMHWVRQA PGKGLEWVAI INFDGSSTYY  60
ADSVRGRFTI SRDNSKNTLY LQMNSLRAED TAVYFCAREL GRRYFDLWGR GTLVSVSS    118

SEQ ID NO: 12           moltype = AA  length = 108
FEATURE                 Location/Qualifiers
source                  1..108
                        mol_type = protein
                        organism = synthetic construct
SEQUENCE: 12
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK              108

SEQ ID NO: 13           moltype = AA  length = 118
FEATURE                 Location/Qualifiers
source                  1..118
                        mol_type = protein
                        organism = synthetic construct
SEQUENCE: 13
QVELVESGGG VVQPGRSQRL SCAASGFTFS SAGMHWVRQA PGKGLEWVAI IWADGSSTYY  60
ADSVRGRFTI SRDNSKNTLY LQMNSLRAED TAVYFCAREL GRRYFDLWGR GTLVSVSS    118

SEQ ID NO: 14           moltype = AA  length = 108
FEATURE                 Location/Qualifiers
source                  1..108
                        mol_type = protein
                        organism = synthetic construct
SEQUENCE: 14
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK              108

SEQ ID NO: 15           moltype = AA  length = 118
FEATURE                 Location/Qualifiers
source                  1..118
                        mol_type = protein
                        organism = synthetic construct
SEQUENCE: 15
QVELVESGGG VVQPGRSQRL SCAASGFTFS SYGMHWVRQA PGKGLEWVAY IWFDGSSTYY  60
ADSVRGRFTI SRDNSKNTLY LQMNSLRAED TAVYFCAREL GRRYFDLWGR GTLVSVSS    118

SEQ ID NO: 16           moltype = AA  length = 108
FEATURE                 Location/Qualifiers
source                  1..108
                        mol_type = protein
                        organism = synthetic construct
SEQUENCE: 16
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKYPPWTFG QGTKVESK              108
```

-continued

```
SEQ ID NO: 17          moltype = AA  length = 118
FEATURE                Location/Qualifiers
source                 1..118
                       mol_type = protein
                       organism = synthetic construct
SEQUENCE: 17
QVELVESGGG VVQPGRSQRL SCAASGFTFS SHGMHWVRQA PGKGLEWVAY IWFDGSSTYY  60
ADSVRGRFTI SRDNSKNTLY LQMNSLRAED TAVYFCAREL GRRYFDLWGR GTLVSVSS    118

SEQ ID NO: 18          moltype = AA  length = 108
FEATURE                Location/Qualifiers
source                 1..108
                       mol_type = protein
                       organism = synthetic construct
SEQUENCE: 18
EIVLTQSPAT LSLSPGERAT LSCRASQSVS SALAWYQQKP GQAPRLLIYD ASKRATGIPA  60
RFSGSGSGTD FTLTISSLEP EDFAVYYCQQ RSKYPPWTFG QGTKVESK              108

SEQ ID NO: 19          moltype = AA  length = 118
FEATURE                Location/Qualifiers
source                 1..118
                       mol_type = protein
                       organism = synthetic construct
SEQUENCE: 19
QVELVESGGG VVQPGRSQRL SCAASGFTFS SHGMHWVRQA PGKGLEWVAT IWFDGSSTYY  60
ADSVRGRFTI SRDNSKNTLY LQMNSLRAED TAVYFCAREL GRRYFDLWGR GTLVSVSS    118

SEQ ID NO: 20          moltype = AA  length = 108
FEATURE                Location/Qualifiers
source                 1..108
                       mol_type = protein
                       organism = synthetic construct
SEQUENCE: 20
EIVLTQSPAT LSLSPGERAT LSCRASQSVS STLAWYQQKP GQAPRLLIYD ASKRATGIPA  60
RFSGSGSGTD FTLTISSLEP EDFAVYYCQQ RSKYPPWTFG QGTKVESK              108

SEQ ID NO: 21          moltype = AA  length = 118
FEATURE                Location/Qualifiers
source                 1..118
                       mol_type = protein
                       organism = synthetic construct
SEQUENCE: 21
QVELVESGGG VVQPGRSQRL SCAASGFTFS SYGMHWVRQA PGKGLEWVAT IWHDGSSTYY  60
ADSVRGRFTI SRDNSKNTLY LQMNSLRAED TAVYFCAREL GRRYFDLWGR GTLVSVSS    118

SEQ ID NO: 22          moltype = AA  length = 108
FEATURE                Location/Qualifiers
source                 1..108
                       mol_type = protein
                       organism = synthetic construct
SEQUENCE: 22
EIVLTQSPAT LSLSPGERAT LSCRASQSVS SALAWYQQKP GQAPRLLIYD ASKRATGIPA  60
RFSGSGSGTD FTLTISSLEP EDFAVYYCQQ RGKYPPWTFG QGTKVESK              108

SEQ ID NO: 23          moltype =   length =
SEQUENCE: 23
000

SEQ ID NO: 24          moltype =   length =
SEQUENCE: 24
000

SEQ ID NO: 25          moltype =   length =
SEQUENCE: 25
000

SEQ ID NO: 26          moltype =   length =
SEQUENCE: 26
000

SEQ ID NO: 27          moltype =   length =
SEQUENCE: 27
000

SEQ ID NO: 28          moltype =   length =
SEQUENCE: 28
000

SEQ ID NO: 29          moltype =   length =
```

-continued

```
SEQUENCE: 29
000

SEQ ID NO: 30           moltype = AA  length = 5
FEATURE                 Location/Qualifiers
source                  1..5
                        mol_type = protein
                        organism = synthetic construct
SEQUENCE: 30
SHGMH                                                                5

SEQ ID NO: 31           moltype = AA  length = 5
FEATURE                 Location/Qualifiers
source                  1..5
                        mol_type = protein
                        organism = synthetic construct
SEQUENCE: 31
STGMH                                                                5

SEQ ID NO: 32           moltype = AA  length = 5
FEATURE                 Location/Qualifiers
source                  1..5
                        mol_type = protein
                        organism = synthetic construct
SEQUENCE: 32
SAGMH                                                                5

SEQ ID NO: 33           moltype = AA  length = 5
FEATURE                 Location/Qualifiers
source                  1..5
                        mol_type = protein
                        organism = synthetic construct
SEQUENCE: 33
SYGMH                                                                5

SEQ ID NO: 34           moltype = AA  length = 17
FEATURE                 Location/Qualifiers
source                  1..17
                        mol_type = protein
                        organism = synthetic construct
SEQUENCE: 34
IIAGDASTTY YADSVRG                                                   17

SEQ ID NO: 35           moltype = AA  length = 17
FEATURE                 Location/Qualifiers
source                  1..17
                        mol_type = protein
                        organism = synthetic construct
SEQUENCE: 35
YIWFDGSSTY YADSVRG                                                   17

SEQ ID NO: 36           moltype = AA  length = 17
FEATURE                 Location/Qualifiers
source                  1..17
                        mol_type = protein
                        organism = synthetic construct
SEQUENCE: 36
IIWADGSSTY YADSVRG                                                   17

SEQ ID NO: 37           moltype = AA  length = 17
FEATURE                 Location/Qualifiers
source                  1..17
                        mol_type = protein
                        organism = synthetic construct
SEQUENCE: 37
IINFDGSSTY YADSVRG                                                   17

SEQ ID NO: 38           moltype = AA  length = 17
FEATURE                 Location/Qualifiers
source                  1..17
                        mol_type = protein
                        organism = synthetic construct
SEQUENCE: 38
IIWFDGSSTY YADSVRG                                                   17

SEQ ID NO: 39           moltype = AA  length = 17
FEATURE                 Location/Qualifiers
source                  1..17
                        mol_type = protein
```

-continued

```
                        organism = synthetic construct
SEQUENCE: 39
TIWHDGSSTY YADSVRG                                                  17

SEQ ID NO: 40           moltype = AA  length = 17
FEATURE                 Location/Qualifiers
source                  1..17
                        mol_type = protein
                        organism = synthetic construct
SEQUENCE: 40
TIWFDGSSTY YADSVRG                                                  17

SEQ ID NO: 41           moltype = AA  length = 9
FEATURE                 Location/Qualifiers
source                  1..9
                        mol_type = protein
                        organism = synthetic construct
SEQUENCE: 41
ELGRRYFDL                                                           9

SEQ ID NO: 42           moltype = AA  length = 9
FEATURE                 Location/Qualifiers
source                  1..9
                        mol_type = protein
                        organism = synthetic construct
SEQUENCE: 42
ELNRRYFDL                                                           9

SEQ ID NO: 43           moltype = AA  length = 11
FEATURE                 Location/Qualifiers
source                  1..11
                        mol_type = protein
                        organism = synthetic construct
SEQUENCE: 43
RASQSVSSAL A                                                        11

SEQ ID NO: 44           moltype = AA  length = 11
FEATURE                 Location/Qualifiers
source                  1..11
                        mol_type = protein
                        organism = synthetic construct
SEQUENCE: 44
RASQSVSSTL A                                                        11

SEQ ID NO: 45           moltype = AA  length = 11
FEATURE                 Location/Qualifiers
source                  1..11
                        mol_type = protein
                        organism = synthetic construct
SEQUENCE: 45
RASQSVSSYL A                                                        11

SEQ ID NO: 46           moltype = AA  length = 7
FEATURE                 Location/Qualifiers
source                  1..7
                        mol_type = protein
                        organism = synthetic construct
SEQUENCE: 46
DASKRAT                                                             7

SEQ ID NO: 47           moltype = AA  length = 10
FEATURE                 Location/Qualifiers
source                  1..10
                        mol_type = protein
                        organism = synthetic construct
SEQUENCE: 47
QQRGKYPPWT                                                          10

SEQ ID NO: 48           moltype = AA  length = 10
FEATURE                 Location/Qualifiers
source                  1..10
                        mol_type = protein
                        organism = synthetic construct
SEQUENCE: 48
QQRSKYPPWT                                                          10

SEQ ID NO: 49           moltype = AA  length = 10
FEATURE                 Location/Qualifiers
source                  1..10
```

-continued

```
                         mol_type = protein
                         organism = synthetic construct
SEQUENCE: 49
QQRSKWPPWT                                                          10

SEQ ID NO: 50            moltype =   length =
SEQUENCE: 50
000

SEQ ID NO: 51            moltype = AA  length = 448
FEATURE                  Location/Qualifiers
source                   1..448
                         mol_type = protein
                         organism = synthetic construct
SEQUENCE: 51
QVELVESGGG VVQPGRSQRL SCAASGFTFS SHGMHWVRQA PGKGLEWVAY IWFDGSSTYY  60
ADSVRGRFTI SRDNSKNTLY LQMNSLRAED TAVYFCAREL GRRYFDLWGR GTLVSVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLYITREPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                      448

SEQ ID NO: 52            moltype = AA  length = 215
FEATURE                  Location/Qualifiers
source                   1..215
                         mol_type = protein
                         organism = synthetic construct
SEQUENCE: 52
EIVLTQSPAT LSLSPGERAT LSCRASQSVS SALAWYQQKP GQAPRLLIYD ASKRATGIPA  60
RFSGSGSGTD FTLTISSLEP EDFAVYYCQQ RSKYPPWTFG QGTKVESKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 53            moltype = AA  length = 5
FEATURE                  Location/Qualifiers
source                   1..5
                         mol_type = protein
                         organism = synthetic construct
VARIANT                  2
                         note = H, Y, A or T
SEQUENCE: 53
SXGMH                                                               5

SEQ ID NO: 54            moltype = AA  length = 17
FEATURE                  Location/Qualifiers
source                   1..17
                         mol_type = protein
                         organism = synthetic construct
VARIANT                  1
                         note = I, T or Y
VARIANT                  3
                         note = W, N or A
VARIANT                  4
                         note = F, H, A or G
VARIANT                  6
                         note = G or A
VARIANT                  8
                         note = S or T
SEQUENCE: 54
XIXXDXSXTY YADSVRG                                                  17

SEQ ID NO: 55            moltype = AA  length = 9
FEATURE                  Location/Qualifiers
source                   1..9
                         mol_type = protein
                         organism = synthetic construct
VARIANT                  3
                         note = G or N
SEQUENCE: 55
ELXRRYFDL                                                           9

SEQ ID NO: 56            moltype = AA  length = 11
FEATURE                  Location/Qualifiers
source                   1..11
                         mol_type = protein
                         organism = synthetic construct
VARIANT                  9
```

-continued

```
                        note = Y, A or T
SEQUENCE: 56
RASQSVSSXL A                                                   11

SEQ ID NO: 57           moltype = AA  length = 10
FEATURE                 Location/Qualifiers
source                  1..10
                        mol_type = protein
                        organism = synthetic construct
VARIANT                 4
                        note = S or G
VARIANT                 6
                        note = Y or W
SEQUENCE: 57
QQRXKXPPWT                                                     10
```